(12) United States Patent
Ceylan et al.

(10) Patent No.: US 10,406,125 B2
(45) Date of Patent: Sep. 10, 2019

(54) COMBINATION COMPRISING AN AMINOTHIOLESTER COMPOUND OR A PHARMACEUTICALLY ACCEPTABLE SALT THEREOF AND A COMPOUND ABLE TO INCREASE THE H2O2 LEVEL IN CANCER CELLS OF A SUBJECT

(71) Applicant: ADVANCED BIODESIGN, Saint-Priest (FR)

(72) Inventors: Ismail Ceylan, Saint-Priest (FR); Gerry Quash, Saint-Priest (FR); Mileidys Perez-Alea, Saint-Priest (FR); Guillaume Martin, Saint-Priest (FR)

(73) Assignee: ADVANCED BIODESIGN, Saint Priest (FR)

( * ) Notice: Subject to any disclaimer, the term of this patent is extended or adjusted under 35 U.S.C. 154(b) by 0 days.

(21) Appl. No.: 15/768,468

(22) PCT Filed: Oct. 14, 2016

(86) PCT No.: PCT/EP2016/074682
§ 371 (c)(1),
(2) Date: Apr. 13, 2018

(87) PCT Pub. No.: WO2017/064241
PCT Pub. Date: Apr. 20, 2017

(65) Prior Publication Data
US 2018/0303773 A1    Oct. 25, 2018

(30) Foreign Application Priority Data

Oct. 15, 2015 (EP) .................................... 15306650

(51) Int. Cl.
| | | |
|---|---|---|
| *A61K 31/145* | (2006.01) |
| *A61K 45/06* | (2006.01) |
| *A61K 31/131* | (2006.01) |
| *A61K 31/136* | (2006.01) |
| *A61K 31/137* | (2006.01) |
| *A61K 31/4453* | (2006.01) |
| *A61K 31/498* | (2006.01) |
| *A61K 31/5375* | (2006.01) |
| *A61K 31/704* | (2006.01) |
| *A61K 33/24* | (2019.01) |
| *A61K 33/36* | (2006.01) |
| *G01N 33/574* | (2006.01) |
| *G01N 33/68* | (2006.01) |
| *G01N 33/84* | (2006.01) |
| *A61P 35/02* | (2006.01) |
| *G01N 21/64* | (2006.01) |

(52) U.S. Cl.
CPC .......... *A61K 31/145* (2013.01); *A61K 31/131* (2013.01); *A61K 31/136* (2013.01); *A61K 31/137* (2013.01); *A61K 31/4453* (2013.01); *A61K 31/498* (2013.01); *A61K 31/5375* (2013.01); *A61K 31/704* (2013.01); *A61K 33/24* (2013.01); *A61K 33/36* (2013.01); *A61K 45/06* (2013.01); *A61P 35/02* (2018.01); *G01N 21/64* (2013.01); *G01N 33/57496* (2013.01); *G01N 33/68* (2013.01); *G01N 33/84* (2013.01); *A61K 2300/00* (2013.01); *G01N 2440/00* (2013.01)

(58) Field of Classification Search
None
See application file for complete search history.

(56) References Cited

U.S. PATENT DOCUMENTS

| | | | |
|---|---|---|---|
| 8,026,231 B2 * | 9/2011 | Fournet .............. | C07D 295/145 514/183 |
| 2007/0032476 A1 | 2/2007 | Fournet et al. | |

FOREIGN PATENT DOCUMENTS

EP    1296946 A1    4/2003

OTHER PUBLICATIONS

International Search Report dated Jan. 18, 2017 during the prosecution of International Application No. PCT/EP2016/074682.
Pelicano et al., "ROS stress in cancer cells and therapeutic implications," Drug Resistance Updates, vol. 7, No. 2, Apr. 2004 (Apr. 2004), pp. 97-110, XP055060447.
Quash et al., "Aldehyde dehydrogenase inhibitors: alpha,beta-Acetylenic N-substituted aminothiolesters are reversible growth inhibitors of normal epithelial but irreversible apoptogens for cancer epithelial cells from human prostate in culture," European Journal of Medicinal Chemistry, Editions Scientifique Elsevier, Paris, FR, vol. 43, No. 5, May 2008 (May 2008), pp. 906-916, XP022639683.
Townsend, A.J., Leone-Kabler, S., Haynes, R.L., Wu, Y., Szweda, L., and Bunting, K.D. (2001). Selective protection by stably transfected human ALDH3A1 (but not human ALDH1A1) against toxicity of aliphatic aldehydes in V79 cells. 130-132, 261-273).
Estrela, J.M., Ortega, A., and Obrador, E. (2006). Glutathione in cancer biology and therapy. Crit. Rev. Clin. Lab. Sci. 43, 143-181.
O'Brien, M.L., and Tew, K.D. (1996). Glutathione and related enzymes in multidrug resistance. Eur. J. Cancer Oxf. Engl. 1990 32A, 967-978.

(Continued)

*Primary Examiner* — Brian J Davis
(74) *Attorney, Agent, or Firm* — Troutman Sanders LLP

(57) ABSTRACT

The present invention relates to a combination comprising an aminothiolester compound or a pharmaceutically acceptable salt thereof, in particular the S-methyl 4-(dimethylamino)-4-methylpent-2-ynethioate or a pharmaceutically acceptable salt thereof, and more particularly the 4-(Dimethylamino)-4-methyl-2-pentynethioic acid S-methyl ester fumarate, and a compound able to increase $H_2O_2$ level in cancer cells of a subject, in particular for use for the treatment of cancer in a subject, wherein cancer cells of said subject do not overproduce $H_2O_2$ in comparison to a control value and have a level of GSH below 5 nmol for 25000 cells.

10 Claims, 9 Drawing Sheets

(56) References Cited

OTHER PUBLICATIONS

Carretero, J., Obrador, E., Esteve, J.M., Ortega, A., Pellicer, J.A., Sempere, F.V., and Estrela, J.M. (2001). Tumoricidal activity of endothelial cells. Inhibition of endothelial nitric oxide production abrogates tumor cytotoxicity induced by hepatic sinusoidal endothelium in response to B16 melanoma adhesion in vitro. J. Biol. Chem. 276, 25775-25782.
Tew, K. and Townsend D (2011) Redox platforms in cancer drug discovery and development. Curr.Opin. Chem.Biol. 15, 156-161.
Aruoma et al., Free Radic Biol Med , (1989) The antioxidant activity of N-acetyl cysteine: its reaction with hydrogen peroxide, hydroxy radical, superoxide anion, and hypochlorous acid:, 6, 593-597.
Zhou Y et al., "Free radical stress in chronic lymphocytic leukemia cells and its role in cellular sensitivity to ROS-generating anticancer agents", Blood, vol. 101, No. 10, May 15, 2003 (May 15, 2003), pp. 4098•4104, XP055245220.
Deavall et al., (2012), Drug-Induced Oxidative Stress and Toxicity., Journal of Toxicology, 2012, e645460.
Pelicano et al., (2003), Inhibition of Mitochondrial Respiration a Novel Strategy to Enhance Drug-Induced Apoptosis in Human Leukemia Cells by a Reactive Oxygen Species-Mediated Mechanism., J. Biol. Chem., 278, 37832-37839.

\* cited by examiner

US 10,406,125 B2

COMBINATION COMPRISING AN AMINOTHIOLESTER COMPOUND OR A PHARMACEUTICALLY ACCEPTABLE SALT THEREOF AND A COMPOUND ABLE TO INCREASE THE H2O2 LEVEL IN CANCER CELLS OF A SUBJECT

CROSS-REFERENCE TO RELATED APPLICATIONS

This is a U.S. national phase application under 35 U.S.C. § 371 of International Patent Application No. PCT/EP2016/074682, filed Oct. 14, 2016, and claims benefit of priority to European Patent Application No. 15306650.1, filed Oct. 15, 2015. The entire contents of these applications are hereby incorporated by reference.

FIELD OF THE INVENTION

The present invention relates to a combination comprising an aminothiolester compound or a pharmaceutically acceptable salt thereof, in particular the S-methyl 4-(dimethylamino)-4-methylpent-2-ynethioate or a pharmaceutically acceptable salt thereof, and more particularly the 4-(Dimethylamino)-4-methyl-2-pentynethioic acid S-methyl ester fumarate, and a compound able to increase $H_2O_2$ level in cancer cells of a subject, in particular for use for the treatment of cancer in a subject, wherein cancer cells of said subject do not overproduce $H_2O_2$ in comparison to a control value and have a level of GSH below 0.5 nmol for 25 000 cells.

BACKGROUND

The redox balance of cells is key to normal cell physiology. It is maintained by 3 systems: GSH/GSSG, NADPH/NADP; Thioredoxin (red)/Thioredoxin (oxd). Of these 3 systems, GSH/GSSG is the most widely studied for its implication in diseased states and for the development of rational therapeutic approaches (Townsend, A. J., Leone-Kabler, S., Haynes, R. L., Wu, Y., Szweda, L., and Bunting, K. D. (2001). Selective protection by stably transfected human ALDH3A1 (but not human ALDH1A1) against toxicity of aliphatic aldehydes in V79 cells. 130-132, 261-273). The diseased states associated with an imbalance in GSH/GSSG include major pathologies like cancers (Estrela, J. M., Ortega, A., and Obrador, E. (2006). Glutathione in cancer biology and therapy. Crit. Rev. Clin. Lab. Sci. 43, 143-181; O'Brien, M. L., and Tew, K. D. (1996). Glutathione and related enzymes in multidrug resistance. Eur. J. Cancer Oxf. Engl. 1990 32A, 967-978). Their one common aetiology is oxidative stress brought about by ROS and/or Reactive Nitrogen Species (RNS) that first cause a decrease in GSH due to the direct detoxification of ROS and RNS. This initial decrease in GSH is followed subsequently by a compensatory increase in GSH synthesis that cells bring into play in order to continue the detoxification of ROS/RNS and of newly formed electrophilic products such as 4-hydroxynonenal (HNE) and malondialdehyde (MDA)) produced by ROS attack on cellular lipids (Esterbauer, H., Schaur, R. J., and Zollner, H. (1991). Chemistry and biochemistry of 4-hydroxynonenal, malonaldehyde and related aldehydes. 11, 81-128).

The GSH paradox in cancer cells is that instead of the deficit in intracellular GSH that would have been expected, it is precisely the opposite that was found experimentally in many different cancer cells (Estrela, J. M., Ortega, A., and Obrador, E. (2006). Glutathione in cancer biology and therapy. Crit. Rev. Clin. Lab. Sci. 43, 143-181). But this increase in GSH has negative therapeutic repercussions as it protects cancer cells from chemo and radio therapies (Carretero, J., Obrador, E., Esteve, J. M., Ortega, A., Pellicer, J. A., Sempere, F. V., and Estrela, J. M. (2001). Tumoricidal activity of endothelial cells. Inhibition of endothelial nitric oxide production abrogates tumor cytotoxicity induced by hepatic sinusoidal endothelium in response to B16 melanoma adhesion in vitro. J. Biol. Chem. 276, 25775-25782).

In addition, if low levels of GSH must be obtained in cancer cells for chemotherapy to be effective, this is not the case for normal cells for not inducing collateral damage thereto.

The therapeutic approaches that are presently being used to lower cellular GSH in order to combat the chemoresistance of cancer cells, target GSH itself or the enzymes involved in GSH synthesis, GSH degradation and GSH efflux. There are already 10 GSH-lowering compounds that are in phases I, II and III of clinical trials as anticancer agents (Tew, K. and Townsend D (2011) Redox platforms in cancer drug discovery and development. Curr. Opin. Chem. Biol. 15, 156-161). They all have to be administered in combination with standard anti-cancer drugs, e.g. cyclophosphamide, taxol, vincristine, melphalan, etc.

Furthermore, the enzymes targeted by these GSH-lowering drugs are those involved in GSH synthesis (gamma glutamyl cysteine ligase), GSH degradation (gamma-glutamyl transpeptidase) and GSH efflux (GSH-S-transferase). These same enzymes are however essential for protecting normal cells from ROS attack. Hence, there is a strong possibility of collateral damage to normal cells as the drugs cannot be delivered selectively to cancer cells and to cancer cells only.

In view of this, there is a need to find other therapeutic solutions which specifically and selectively target GSH in cancer cells.

The inventors of the present invention have unexpectedly found that a combination comprising an aminothiolester compound or a pharmaceutically acceptable salt thereof, in particular the S-methyl 4-(dimethylamino)-4-methylpent-2-ynethioate or a pharmaceutically acceptable salt thereof, and more particularly the 4-(Dimethylamino)-4-methyl-2-pentynethioic acid S-methyl ester fumarate, and a compound able to increase the $H_2O_2$ level in cancer cells of a subject, is useful as a medicament and able to treat cancer in a subject, wherein cancer cells of said subject do not overproduce $H_2O_2$. In particular, they found that a combination comprising an aminothiolester compound or a pharmaceutically acceptable salt thereof, in particular the S-methyl 4-(dimethylamino)-4-methylpent-2-ynethioate or a pharmaceutically acceptable salt thereof, and more particularly the 4-(Dimethylamino)-4-methyl-2-pentynethioic acid S-methyl ester fumarate, and a compound able to increase the $H_2O_2$ level in cancer cells of a subject, is useful as a medicament and able to treat cancer in a subject, wherein cancer cells of said subject do not overproduce $H_2O_2$ and have a level of GSH below 0.5 nmol for 25 000 cells.

Without being bound by any theory, when the compound able to increase the $H_2O_2$ level in cancer cells of a subject would have induced an increase in $H_2O_2$ level in the cancer cells, then the aminothiolester compound or a pharmaceutically acceptable salt thereof, would increase the levels of intra cellular metabolites that are produced by $H_2O_2$ attack, and, at the same time, GSH would thus be consumed in the detoxification of these electrophilic metabolites. As a result, insufficient GSH would be available in cancer cells to act as a scavenger of $H_2O_2$. Hence, levels of $H_2O_2$ should increase and should trigger-off the $H_2O_2$-dependent mechanisms in the mitochondrial (intrinsic) pathway of apoptosis.

In normal cells that have not undergone initially an attack by $H_2O_2$, intracellular GSH levels are already high (due to the absence of $H_2O_2$) so that the levels of any $H_2O_2$-induced electrophiles are below those in their cancer counterparts. However, $H_2O_2$ levels in normal cells can concomitantly rise when a compound able to increase the $H_2O_2$ level in cancer cells of a subject is used, if this compound is able to increase the level of $H_2O_2$ in both normal and cancer cells. In this latter case, $H_2O_2$ levels in normal cells will however still be lower than those in cancer cells and will thus remain below their apoptotic threshold upon treatment with the aminothiolester compound according to the invention or a pharmaceutically acceptable salt thereof.

SUMMARY

As previously mentioned, the inventors of the present invention have unexpectedly found that an aminothiolester compound or a pharmaceutically acceptable salt thereof, in particular the S-methyl 4-(dimethylamino)-4-methylpent-2-ynethioate or a pharmaceutically acceptable salt thereof in combination with a compound able to increase the $H_2O_2$ level in cancer cells of a subject, is useful as a medicament and able to treat cancer in a subject, wherein cancer cells of said subject do not overproduce the $H_2O_2$. In particular, they found that a combination comprising an aminothiolester compound or a pharmaceutically acceptable salt thereof, in particular the S-methyl 4-(dimethylamino)-4-methylpent-2-ynethioate or a pharmaceutically acceptable salt thereof, and more particularly the 4-(Dimethylamino)-4-methyl-2-pentynethioic acid S-methyl ester fumarate, and a compound able to increase the $H_2O_2$ level in cancer cells of a subject, is useful as a medicament and able to treat cancer in a subject, wherein cancer cells of said subject do not overproduce $H_2O_2$ and have a level of GSH below 0.5 nmol for 25 000 cells.

This new therapy presents the advantage that normal cells suffer less collateral damage because their initial electrophilic metabolites are so low (due to the absence of $H_2O_2$) that they will anyway remain below their apoptotic threshold upon treatment with an aminothiolester compound according to the invention or a pharmaceutically acceptable salt thereof.

The present invention thus relates to a combination comprising a compound of formula (I):

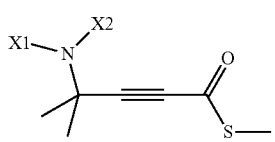

(I)

wherein X1 and X2, identical or different, are chosen among a $C_1$-$C_7$ alkyl group, a phenyl, a benzyl, or X1 and X2 together with the nitrogen atom to which they are linked form an heterocycle, in particular a piperidine or a morpholine;

or a pharmaceutical acceptable salt thereof and a compound able to increase the $H_2O_2$ level in cancer cells of a subject, for use for the treatment of cancer in a subject.

More particularly, it relates to a combination comprising a compound of formula (I):

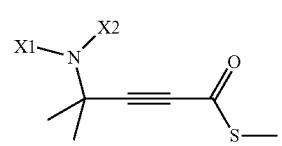

(I)

wherein X1 and X2, identical or different, are chosen among a $C_1$-$C_7$ alkyl group, a phenyl, a benzyl, or X1 and X2 together with the nitrogen atom to which they are linked form an heterocycle, in particular a piperidine or a morpholine;

or a pharmaceutical acceptable salt thereof; and a compound able to increase the $H_2O_2$ level in cancer cells of a subject, for use for the treatment of cancer in a subject, wherein cancer cells of said subject:

do not overproduce $H_2O_2$ in comparison to a control value, and have a level of GSH below 0.5 nmol for 25 000 cells.

In particular, cancer cells of said subject have also a MDA-adducts level above 75 ng per µg of total protein and/or a HNE-adducts level above 1 µg per µg of total protein, after in vitro treatment with a compound of formula (I) or a pharmaceutical acceptable salt thereof.

The present invention also relates to products comprising a compound of formula (I):

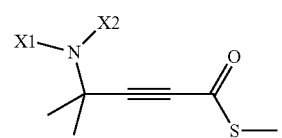

(I)

wherein X1 and X2, identical or different, are chosen among a $C_1$-$C_7$ alkyl group, a phenyl, a benzyl, or X1 and X2 together with the nitrogen atom to which they are linked form an heterocycle, in particular a piperidine or a morpholine;

or a pharmaceutical acceptable salt thereof; and a compound able to increase the $H_2O_2$ level in cancer cells of a subject as a combined preparation for use spread out over time for the treatment of cancer in a subject, wherein cancer cells of said subject:

do not overproduce $H_2O_2$ in comparison to a control value, and have a level of GSH below 0.5 nmol for 25 000 cells.

In particular, cancer cells of said subject have also a MDA-adducts level above 75 ng per µg of total protein and/or a HNE-adducts level above 1 µg per µg of total protein, after in vitro treatment with a compound of formula (I) or a pharmaceutical acceptable salt thereof.

In particular, said subject is identified by measuring the $H_2O_2$ level and the GSH level in cancer cells of said subject.

More particularly, said $H_2O_2$ level is determined by quantifying the level of Fluorescence Intensity.

The present invention also relates to a pharmaceutical composition comprising a compound of formula (I):

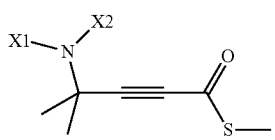

(I)

wherein X1 and X2, identical or different, are chosen among a $C_1$-$C_7$ alkyl group, a phenyl, a benzyl, or X1 and X2 together with the nitrogen atom to which they are linked form an heterocycle, in particular a piperidine or a morpholine;

or a pharmaceutical acceptable salt thereof and a compound able to increase the $H_2O_2$ level in cancer cells of a subject.

The present invention further relates to a method for selecting a subject suffering from a cancer and who will most likely benefit from a treatment with a combination comprising a compound of formula (I):

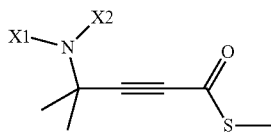

(I)

wherein X1 and X2, identical or different, are chosen among a $C_1$-$C_7$ alkyl group, a phenyl, a benzyl, or X1 and X2 together with the nitrogen atom to which they are linked form an heterocycle, in particular a piperidine or a morpholine;

or a pharmaceutical acceptable salt thereof and a compound able to increase the $H_2O_2$ level in cancer cells of a subject wherein said method comprises:
a) measuring the $H_2O_2$ level in a cancer cells sample of said subject;
b) comparing the resulting level of step a. with a control value; and
c) measuring the GSH level in a cancer cells sample of said subject;
wherein:
a $H_2O_2$ level of said cancer cells sample of said subject not higher than the control value, and
a GSH level of said cancer cells sample of said subject below 0.5 nmol for 25 000 cells,
indicates that the subject is likely to benefit from a treatment with a combination comprising a compound of formula (I), or a pharmaceutically acceptable salt thereof and a compound able to increase the $H_2O_2$ level in cancer cells of of a subject.

In one embodiment, said method comprises:
a) measuring the $H_2O_2$ level in a cancer cells sample of said subject;
b) comparing the resulting level of step a. with a control value;
c) measuring the GSH level in a cancer cells sample of said subject; and/or
d) measuring the MDA-adducts and/or HNE-adducts level after an in vitro treatment with a compound of formula (I) or a pharmaceutical acceptable salt thereof according to the invention in a cancer cells sample of said subject;
wherein:

a $H_2O_2$ level of said cancer cells sample of said subject not higher than the control value,
a GSH level of said cancer cells sample of said subject below 0.5 nmol per 25 000 cells, and/or
a MDA-adducts level above 75 ng per μg of total protein and/or a HNE-adducts level above 1 μg per μg of protein,
indicates that the subject is likely to benefit from a treatment with a combination according to the invention.

As described herein, "$H_2O_2$" means "hydrogen peroxide" and is a well-known by the man skilled in the art. It represents chemically reactive molecules containing oxygen. It is formed as a natural byproduct of the normal metabolism of oxygen and has important roles in cell signaling and homeostasis. However, during times of environmental stress (e.g., UV or heat exposure), it levels can increase dramatically. This may result in significant damage to cell structures. Cumulatively, this is known as oxidative stress. Hydrogen peroxide are also generated by exogenous sources such as ionizing radiation.

In particular, a $H_2O_2$ level not higher than a value comprised between 2 000 and 400 000 Relative Fluorescence Intensity, for example between 10 000 and 100 000 Relative Fluorescence Intensity or 15 000 and 100 000 Relative Fluorescence Intensity, and more particularly a $H_2O_2$ level not higher than 20 000 Relative Fluorescence Intensity, even more particularly not higher than 21 598 Relative Fluorescence Intensity, indicates that the subject is likely to benefit from a treatment with a combination according to the invention.

In particular, the level not higher than a value comprised between 2 000 and 400 000 Relative Fluorescence Intensity, for example between 10 000 and 100 000 Relative Fluorescence Intensity or 15 000 and 100 000 Relative Fluorescence Intensity, and more particularly a $H_2O_2$ level not higher than 20 000 Relative Fluorescence Intensity, even more particularly not higher than 21 598 Relative Fluorescence Intensity, is measured with the Total ROS/superoxide detection kit (Enzo life science), more particularly as measured on an Appliskan fluorescence microplate reader (Thermo Scientific) (Ex/Em=488/520 nm and Ex/Em=550/610 nm).

If the cut-off level of $H_2O_2$ is given here and elsewhere in the description by measuring the fluorescence intensity, this method is nonexclusive and the cut-off level of $H_2O_2$ can be determined by any other method available to the man skilled in the art, the parameter determining where to put the cut-off being the correlation between the $IC_{50}$ of the product according to the invention and the level of $H_2O_2$. The $IC_{50}$ is a measure well-known to the man skilled in the art.

As described herein, "GSH" means "Glutathione" and is well known by the man skilled in the art. It is a tripeptide with a gamma peptide linkage between the carboxyl group of the glutamate side chain and the amine group of cysteine, and the carboxyl group of cysteine is attached by normal peptide linkage to a glycine.

In particular, in the scope of the present invention, the GSH level is below 0.5 nmol for 25 000 cells, in particular below 0.45 nmol for 25 000 cells and more particularly below 0.4 nmol for 25 000 cells.

The level of GSH is determined by any method available to the man skilled in the art. For example, the level of GSH is determined by luminescence, for example with the Promega GSH-Glo kit (Promega).

If the cut-off level of GSH is given here and elsewhere in the description by luminescence, this method is nonexclusive and the cut-off level of GSH can be determined by any other method available to the man skilled in the art As described herein, "MDA" is used for "Malondialdehyde", an organic compound with the formula $CH_2(CHO)_2$. This reactive species is well known by the man skilled in the art and occurs naturally and is a marker lipids peroxidation in cells. In addition, a "MDA-adduct" according to the invention is an adduct formed between MDA and the proteins of the cancer cells as well as with the DNA of the cancer cells.

In particular, in the scope of the present invention, the MDA-adducts level after an in vitro treatment with a compound of formula (I) according to the invention of a pharmaceutical acceptable salt thereof is above 75 ng per µg of total protein, in particular above 90 ng per µg of total protein and more particularly above 100 ng per µg of total protein. The level of MDA-adducts is determined by any method available to the man skilled in the art. For example, the level of MDA-adducts is determined by immuno-monitoring, for example with OxiSelect™ MDA-adduct competitive ELISA kit (CELL BIOLABS).

As described herein, "HNE" is used for "4-hydroxy-2-nonenal", an organic compound of formula $C_9H_{16}O_2$. This reactive species is well known by the man skilled in the art and occurs naturally and is a marker lipids peroxidation in cells.

In addition, a "HNE-adduct" according to the invention is an adduct formed between HNE and the proteins of the cancer cells as well as an adduct formed with the GSH of the cancer cells.

In particular, in the scope of the present invention, the HNE-adducts level after an in vitro treatment with a compound of formula (I) according to the invention or a pharmaceutical acceptable salt thereof is above 750 ng per µg of total protein, in particular above 900 ng per µg of total protein and more particularly above 1 µg per µg of total protein.

The level of HNE-adducts is determined by any method available to the man skilled in the art. For example, the level of HNE-adducts is determined by immuno-monitoring, for example with OxiSelect™ HNE-adduct competitive ELISA kit (CELL BIOLABS).

By "total protein" is meant the content of total protein of the cancer cell.

By "in vitro treatment with a compound of formula (I) according to the invention or a pharmaceutical acceptable salt thereof" is meant that the level of MDA-adducts and/or of HNE-adducts is measured after a step of treatment, in vitro, on a cancer cells sample of the subject, for example at the conditions described in the experimental section, taking into account that the doses of a compound of formula (I) according to the invention of a pharmaceutical acceptable salt thereof which can be administered are until 60 µM.

By a "$C_1$-$C_7$ alkyl group" is meant an aliphatic-hydrocarbon group which may be straight or branched having 1 to 7 carbon atoms in the chain unless specified otherwise. In particular, alkyl groups have 1 to 3 carbon atoms in the chain ($C_1$-$C_3$ alkyl). Branched means that one or more alkyl groups such as methyl, ethyl or propyl are attached to a linear alkyl chain. Exemplary alkyl groups include methyl, ethyl, n-propyl, i-propyl, n-butyl, t-butyl, 2,2-dimethylbutyl, n-pentyl, n-hexyl, octyl, in particular methyl.

In particular, the compound of formula (I) is a compound as mentioned above wherein X1 and X2, identical or different, are chosen among a methyl, a phenyl, a benzyl, at least one of X1 or X2 being a methyl, or wherein X1 and X2 together with the nitrogen atom to which they are linked form a piperidine or a morpholine.

More particularly, said compound is chosen from:
S-methyl 4-methyl-4-(piperidin-1-yl)pent-2-ynethioate;
S-methyl 4-[benzyl(methyl)amino]-4-methylpent-2-ynethioate;
S-methyl 4-methyl-4-[methyl(phenyl)amino]pent-2-ynethioate;
S-methyl 4-methyl-4-(morpholin-4-yl)pent-2-ynethioate; and
S-methyl 4-(dimethylamino)-4-methylpent-2-ynethioate.

These compounds are further described in Table 1 below.

TABLE 1

| IUPAC Name | Formula | |
|---|---|---|
| S-methyl 4-methyl-4-(piperidin-1-yl)pent-2-ynethioate | [structure] | Formula Weight: 225.4 Formula: $C_{12}H_{19}NOS$ |
| S-methyl 4-[benzyl(methyl)amino]-4-methylpent-2-ynethioate | [structure] | Formula Weight: 261.4 Formula: $C_{15}H_{19}NOS$ |
| S-methyl 4-methyl-4-[methyl(phenyl)amino]pent-2-ynethioate | [structure] | Formula Weight: 247.4 Formula: $C_{14}H_{17}NOS$ |
| S-methyl 4-methyl-4-(morpholin-4-yl)pent-2-ynethioate | [structure] | Formula Weight: 227.3 Formula: $C_{11}H_{17}NO_2S$ |
| S-methyl 4-(dimethylamino)-4-methylpent-2-ynethioate | [structure] | Formula Weight: 185.28 Fumarate Salt: 301.2 Formula: $C_9H_{15}NOS$ |

In a preferred embodiment, said compound is the S-methyl 4-(dimethylamino)-4-methylpent-2-ynethioate.

These compounds can be prepared according to methods well known by the man skilled in the art. In particular, these compounds can be prepared from the corresponding acetylenic amine treated successively by BuLi, COS and MeI. A detailed process of preparation can be found for example in G. Quash et al., European Journal of Medicinal Chemistry 43 (2008) 906-916, from which the content is incorporated by reference, in particular in the part 2 of the Material and Methods section.

S-methyl 4-(dimethylamino)-4-methylpent-2-ynethioate (CAS number 350229-29-7, formula weight: 185.29 g·mol$^{-1}$, formula: $C_9H_{15}NOS$), also known under DIMATE is a compound of formula (II):

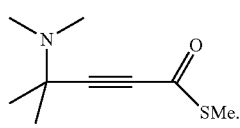
(II)

This compound and its process of preparation are described in the patent EP1296946 (in particular in example 1), from which the content is incorporated by reference.

By a "pharmaceutically acceptable salt" of a compound of formula (I), it is meant that the compound is modified by making acid or base salts thereof. The pharmaceutically acceptable salts include the conventional non-toxic salts or the quaternary ammonium salts of the compound, for example, from non-toxic inorganic or organic acids. For example, such conventional non-toxic salts include those such as fumarate, phosphate, citrate, chlorydrate, and the like. The pharmaceutically acceptable salts of of a compound of formula (I) can be synthesized from the parent compound by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418.

In particular, the compound of formula (I) is the S-methyl 4-(dimethylamino)-4-methylpent-2-ynethioate and its pharmaceutically acceptable salt is its fumarate salt i.e. the 4-(Dimethylamino)-4-methyl-2-pentynethioic acid S-methyl ester fumarate (formula weight: 301.4 g·mol$^{-1}$, formula: $C_{13}H_{19}NO_5S$). Such fumarate salt can be prepared from S-methyl 4-(dimethylamino)-4-methylpent-2-ynethioate in anhydrous ether with addition of a solution of fumaric acid in anhydrous ethanol. The mono-fumarate salt is collected by filtration, washed with ether and dried.

In the scope of the invention, an aminothiolester compound, a compound of formula (I) or a pharmaceutically acceptable salt thereof, S-methyl 4-(dimethylamino)-4-methylpent-2-ynethioate or a pharmaceutical acceptable salt thereof, in particular 4-(Dimethylamino)-4-methyl-2-pentynethioic acid S-methyl ester fumarate, will be used interchangeably with the term "compound according to the invention".

Compounds able to increase the $H_2O_2$ level in cancer cells of a subject are known by the man skilled in the art. In particular, in the scope of the invention, these compounds are able to selectively increase the $H_2O_2$ level in cancer cells of a subject i.e. are compounds that are able to increase the $H_2O_2$ level in cancer cells of a subject but that, at the same time, do not increase the $H_2O_2$ level of non-cancer cells (i.e. normal cells) of that subject. The use of these compounds that shows a selective action on cancer cells allows to avoid side effects like cytostatic effect on normal cells. Compounds able to increase the $H_2O_2$ level can be chosen among pyocyanin, 2-methoxyestradiol, rotenone, $As_2O_3$ (Arsenic Trioxyde), doxorubicin, daunorubicin, AZT, diclofenac, paracetamol, cisplatin, chlorpromazine, piperlongumine, etoposide, mitoxanthrone and parthenolide (Deavall et al., (2012), Drug-Induced Oxidative Stress and Toxicity., *Journal of Toxicology*, 2012, e645460; Pelicano et al., (2003), Inhibition of Mitochondrial Respiration A NOVEL STRATEGY TO ENHANCE DRUG-INDUCED APOPTOSIS IN HUMAN LEUKEMIA CELLS BY A REACTIVE OXYGEN SPECIES-MEDIATED MECHANISM, *J. Biol. Chem.*, 278, 37832-37839). More particularly, said compound is chosen from pyocyanin, 2-methoxyestradiol, rotenone, $As_2O_3$, doxorubicin, daunorubicin, AZT, diclofenac, paracetamol, chlorpromazine, piperlongumine, etoposide, mitoxanthrone and parthenolide. Preferably said compound is the $As_2O_3$ (Arsenic trioxide) or the daunorubicin. These compounds are commercially available or can be prepared using well known methods of preparation.

The terms "treat", "treating", "treated" or "treatment", as used herein, refer to therapeutic treatment wherein the object is to eliminate or lessen symptoms. Beneficial or desired clinical results include, but are not limited to, elimination of symptoms, alleviation of symptoms, diminishment of extent of condition, stabilized (i.e., not worsening) state of condition, delay or slowing of progression of the condition, to the prevention of the onset, recurrence or spread of a disease or disorder, or of one or more symptoms thereof. In certain embodiments, the terms refer to the treatment with or administration of compounds provided herein prior to the onset of symptoms. The terms encompass the inhibition or reduction of a symptom of the particular disease. Subjects with familial history of a disease in particular are candidates for treatment regimens in certain embodiments. Also, subjects in whom a genetic disposition for the particular disease has been shown are candidates for treatment regimens in certain embodiments. In addition, subjects who have a history of recurring symptoms are also potential candidates for the treatment. In this regard, the term "treatment" may be interchangeably used with the term "prophylactic treatment."

As used herein and unless otherwise defined, "cancer" refers to the growth, division or proliferation of abnormal cells in the body. Cancers according to the invention are cancers in which an overproduction of $H_2O_2$ is not observed in comparison to a control value, in particular cancers in which there are both not an overproduction of $H_2O_2$ observed in comparison to a control value and a level of GSH below 0.5 nmol for 25 000 cells. Such cancers include, but are not limited to leukemia, lymphomas, blood cancer, breast cancer (in particular TNBC), lung cancer (in particular EGFR mutated), melanomas, colon cancer, pancreas cancer, ovarian cancer, osteosarcoma, brain cancer, bladder cancer and gastric cancer.

As such, the present invention also relates to a combination comprising a compound of formula (I) or a pharmaceutically acceptable salt thereof, in particular the S-methyl 4-(dimethylamino)-4-methylpent-2-ynethioate or a pharmaceutically acceptable salt thereof, and more particularly the 4-(Dimethylamino)-4-methyl-2-pentynethioic acid S-methyl ester fumarate, and a compound able to increase the $H_2O_2$ level in cancer cells of a subject, for use according to the invention, to products for use according to the invention or to methods according to the invention, wherein the cancer to treat is chosen from leukemia, lymphomas, blood cancer, breast cancer (in particular TNBC), lung cancer (in particular EGFR mutated), melanomas, colon cancer, pancreas cancer, ovarian cancer, osteosarcoma, brain cancer, bladder cancer and gastric cancer.

Still particularly, said cancer is a chemoresistant and/or radioresistant cancer.

By "chemoresistant" is meant, a cancer as described herein against which chemotherapy doesn't work or stop working.

By "radioresistant" is meant, a cancer as described herein against which radiotherapy doesn't work or stop working.

In particular, said cancer is a cancer in which a MDA-adducts level above 75 ng per µg of total protein and/or a HNE-adducts level above 1 µg per µg of total protein, after in vitro treatment with a compound of formula (I) of a pharmaceutical acceptable salt thereof is observed.

As used herein, the term "subject" refers to a warm-blooded animal such as a mammal, animal or human, in particular a human, which is afflicted with, or has the potential to be afflicted with one or more diseases and conditions described herein, and more particularly, in whom cancer cells do not overproduce the $H_2O_2$ in comparison to a control value, and even more particularly in whom cancers cells both do not overproduce $H_2O_2$ in comparison to a control value and have a level of GSH below 0.5 nmol for 25 000 cells. Still particularly, cancer cells of said subject that do not overproduce $H_2O_2$ in comparison to a control value and have a level of GSH below 0.5 nmol for 25 000 cells are chemoresistant and/or radioresistant cancer cells. Even more particularly, cancer cells of said subject that do not overproduce $H_2O_2$ in comparison to a control value, more particularly that both do not overproduce $H_2O_2$ in comparison to a control value and have a level of GSH below 0.5 nmol for 25 000 cells, have also a MDA-adducts level above 75 ng per µg of total protein and/or a HNE-adducts level above 1 µg per µg of total protein after in vitro treatment with a compound of formula (I) or a pharmaceutical acceptable salt thereof.

The terms "not overproduce", "no overproduction", as used herein, describe a situation, where in a diseased cell or tissue, a compound is not produced in overabundance compared to a corresponding control cell or tissue named control value. It refers to a production of $H_2O_2$ in cancer cells which is not higher than i.e. lower than or equal to the production of $H_2O_2$ in a corresponding control cell or tissue named control value.

In particular, the present invention thus relates to a combination for use according to the invention or to products for use according to the invention, wherein said subject is identified by measuring the $H_2O_2$ level in cancer cells of said subject.

The level of $H_2O_2$ may be, for instance, measured by any method known to the skilled person, such as, for example, by determining the level of Relative Fluorescence Intensity, which can be done for example thanks to the Total ROS/superoxide detection kit (Enzo life science), in particular as measured on Appliskan fluorescence microplate reader (Thermo Scientific) (Ex/Em=488/520 nm and Ex/Em=550/610 nm).

In particular, the present invention thus relates to a combination for use according to the invention or to products for use according to the invention, wherein said $H_2O_2$ level is determined by quantifying the level of Fluorescence Intensity.

More particularly, it relates to a combination for use according to the invention or to products for use according to the invention, wherein said $H_2O_2$ level is not higher than a value comprised between 2 000 and 400 000 Relative Fluorescence Intensity, for example between 10 000 and 100 000 Relative Fluorescence Intensity or 15 000 and 100 000 Relative Fluorescence Intensity, and more particularly a $H_2O_2$ level not higher than 20 000 Relative Fluorescence Intensity, even more particularly not higher than 21 598 Relative Fluorescence Intensity.

The skilled person will readily appreciate that any other parameter suitable for determining the $H_2O_2$ level of cells can be used in conjunction with the present invention.

Accordingly, any other methods known by the person skilled in the art to detect the level of $H_2O_2$ can be used without departing from the scope of the invention.

In particular, the present invention thus relates to a combination for use according to the invention or to products for use according to the invention, wherein said $H_2O_2$ level is determined by quantifying the level of Fluorescence Intensity thanks to the Total ROS/superoxide detection kit (Enzo life science), more particularly as measured on Appliskan fluorescence microplate reader (Thermo Scientific) (Ex/Em=488/520 nm and Ex/Em=550/610 nm).

If the method used in the experimental part is a determination of the level of $H_2O_2$ by mean fluorescence intensity, it is again stated that this method is nonexclusive and that the level of $H_2O_2$ can be determined by any other method available to the man skilled in the art.

The level of GSH is determined by any method available to the man skilled in the art. For example, the level of GSH is determined by luminescence, for example with the Promega GSH-Glo kit (Promega).

The skilled person will readily appreciate that any other parameter suitable for determining the GSH level of cells can be used in conjunction with the present invention.

Accordingly, any other methods known by the person skilled in the art to detect the level of GSH can be used without departing from the scope of the invention.

In particular, the present invention thus relates to the compound for use according to the invention, wherein said GSH level is determined by luminescence, more particularly with the Promega GSH-Glo kit (Promega).

The level of MDA-adducts is determined by any method available to the man skilled in the art. For example, the level of MDA-adducts is determined by immuno-monitoring, for example with OxiSelect™ MDA-adduct competitive ELISA kit (CELL BIOLABS).

The skilled person will readily appreciate that any other parameter suitable for determining the MDA-adducts level of cells can be used in conjunction with the present invention.

Accordingly, any other methods known by the person skilled in the art to detect the level of MDA-adducts can be used without departing from the scope of the invention.

In one embodiment, the level of MDA-adducts is thus measured after an in vitro treatment with a compound of formula (I) according to the invention or a pharmaceutical acceptable salt thereof.

The level of HNE-adducts is determined by any method available to the man skilled in the art. For example, the level of HNE-adducts is determined by immuno-monitoring, for example with OxiSelect™ HNE-adduct competitive ELISA kit (CELL BIOLABS).

The skilled person will readily appreciate that any other parameter suitable for determining the HNE-adducts level of cells can be used in conjunction with the present invention.

Accordingly, any other methods known by the person skilled in the art to detect the level of HNE-adducts can be used without departing from the scope of the invention.

In one embodiment, the level of HNE-adducts is thus measured after an in vitro treatment with a compound of formula (I) according to the invention or a pharmaceutical acceptable salt thereof.

As used herein, the term "sample" means a substance of biological origin. Examples of biological samples include, but are not limited to bodily fluids samples and biopsy. Bodily fluids include blood, urine, saliva or any other bodily secretion or derivative thereof. As used herein "blood" includes whole blood, plasma, serum, circulating epithelial cells, constituents, or any derivative of blood. The biological sample according to the invention may be obtained from the subject by any appropriate means of sampling known from the person skilled in the art.

For determining the level of $H_2O_2$, the level of GSH and/or the level of MDA-adducts and/or HNE adducts in cancer cells, the sample is in particular a biopsy of tumor, e.g. of a leukemia tumor, lymphoma tumor, blood tumor, breast tumor (in particular TNBC), lung tumor (in particular EGFR mutated), melanoma tumor, colon tumor, pancreatic tumor, ovarian tumor, osteosarcoma tumor, brain tumor, bladder tumor or gastric tumor.

As regards to the comparison of level of $H_2O_2$, preferably the control value is measured in a sample of the same tissue origin as the sample of the cancer cells or the cancer sample, and more preferably in a sample of the same tissue origin as the sample of the cancer cells or the cancer sample of the same subject.

Preferably, the "control value" corresponds to the normal level of $H_2O_2$.

As intended herein a "normal level" of $H_2O_2$ means that the level of $H_2O_2$ in the sample is within the norm cut-off values for $H_2O_2$. The norm is dependent on the sample type and on the method used for measuring the level of $H_2O_2$ in the sample. In particular, the reference value of $H_2O_2$ may thus correspond to the absence of, or to a basal level of $H_2O_2$ in normal cells, preferably of the same tissue, and more preferably of the same tissue of the same subject or to the $H_2O_2$ value in cancer cells incubated with NAC preferably of the same tissue, and more preferably of the same tissue of the same subject.

NAC is an avid scavenger of hydroxy radicals (rate constant: $1.36 \times 10^{10}$ $M^{-1}, s^{-1}$) but which reacts slowly with hydrogen peroxide (rate constant: $0.38 \times M^{-1}$, $s^1$) and shows no reaction with superoxide anion (Aruoma et al; Free Radic Biol Med, (1989) The antioxidant activity of N-acetyl cysteine: its reaction with hydrogen peroxide, hydroxy radical, superoxide anion, and hypochlorous acid: 6, 593-597).

A level is considered to be statistically lower or equal if the level of $H_2O_2$ in the cancer sample of the subject is decreased to below the normal level of $H_2O_2$ or is equal to the normal level of $H_2O_2$. In particular, the level of $H_2O_2$ is considered to be statistically lower if the level of $H_2O_2$ in the cancer sample of the patient is decreased by order of at least 5 or 10 or 15 or 20 or 25 or 30 or 35 or 40 or 45 or 50 or 60 or 70 or 80 or 90 or 100 or 200 or 300 or 400 or 500 or 600% compared with the control value of level of $H_2O_2$.

In the same manner, a level is considered to be not overproduced if the level of $H_2O_2$ in the cancer sample of the subject is equal to the normal level of $H_2O_2$ or is decreased to below the normal level of $H_2O_2$, more particularly decreased by order of at least 5 or 10 or 15 or 20 or 25 or 30 or 35 or 40 or 50 or 60 or 70 or 80 or 90 or 100 or 200 or 300 or 400 or 500 or 600% compared with the control value of level of $H_2O_2$.

A level is considered to be statistically lower or equal if the level of $H_2O_2$ in the cancer sample of the subject is equal to the level of $H_2O_2$ in cancer cells incubated with NAC or decreased to below the level of $H_2O_2$ in cancer cells incubated with NAC. In particular, the level of $H_2O_2$ is considered to be statistically lower if the level of $H_2O_2$ in the cancer sample of the patient is decreased by order of at least 5 or 10 or 15 or 20 or 25 or 30 or 35 or 40 or 50 or 60 or 70 or 80 or 90 or 100 or 200 or 300 or 400 or 500 or 600% compared with the value of level of $H_2O_2$ of the cancer sample incubated with NAC, preferably of the same tissue, and more preferably of the same tissue of the same subject.

In the same manner, a level is considered to be not overproduced if the level of $H_2O_2$ in the cancer sample of the subject is equal to the normal level of $H_2O_2$ or is decreased to below the level of $H_2O_2$ in the cancer cells incubated with NAC, more particularly decreased by order of at least 5 or 10 or 15 or 20 or 25 or 30 or 35 or 40 or 45 or 50 or 60 or 70 or 80 or 90 or 100 or 200 or 300 or 400 or 500 or 600% compared with the control value of level of $H_2O_2$.

The control value(s) may be determined as a single value or a range of values which is determined based on the level of $H_2O_2$ measured in a population of control cells i.e. normal cells, in particular in a population of normal cells of the same tissue origin as cancer cells, and more particularly from the same subject, or i.e. of cancer cells incubated with NAC, in particular in a population of cancer cells incubated with NAC, of the same tissue origin, and more particularly from the same subject.

The control value may therein be a predetermined value or a value that is determined together with the measurement value.

Typically, the analysed population could be divided into quantiles based on the measured level of $H_2O_2$. The control value could be defined as the median, or the second tertile, or the second or third quartile, or the third or fourth quintile etc.

The control value of $H_2O_2$ may vary depending on the method used for measuring. In one embodiment, when the cancer to treat is a leukaemia, the reference value is determined using the level of $H_2O_2$ in HL60 cells. The HL60 cell line is an established Human promyelocytic leukemia cell line well known by the man skilled in the art.

In particular, in said embodiment, the level of $H_2O_2$ is considered to be statistically equal to or lower than or to be not overproduced if "y" is not higher than 2x/3, "x" being the level of $H_2O_2$ in the HL60 cells, and "y" being the level of $H_2O_2$ in the cancer sample of the subject.

The control value(s) may be determined as a single value or a range of values which is determined based on the level of $H_2O_2$ measured in a population of control cells i.e. HL60 cells.

Typically, the analysed population could be divided into quantiles based on the measured level of $H_2O_2$. The control value could be defined as the median, or the second tertile, or the second or third quartile, or the third or fourth quintile etc. The control value of $H_2O_2$ may vary depending on the method used for measuring.

The same method of comparison as the one described for HL60 cells when the cancer to teat is a leukaemia applies for the type of cancers mentioned in the table 2 below with the following corresponding cell lines as referenced values.

TABLE 2

| Type of cancer | Referenced Cell line |
| --- | --- |
| Bladder | HT-1197 |
| Blood | HL-60 |
| Brain | CGL-1 |
| Breast | MDA-MB-231 |
| Colon | Lovo |
| Head & Neck | Fadu |

The present invention further relates to a method of treatment of cancer in a subject, in particular wherein cancer cells of said subject do not overproduce the $H_2O_2$ in comparison to a control value, and in particular do not overproduce $H_2O_2$ in comparison to a control value and have a level of GSH below 0.5 nmol for 25 000 cells, said method comprising the administration of a therapeutically effective amount of a combination comprising a compound of formula (I) or a pharmaceutically acceptable salt thereof, in particular the S-methyl 4-(dimethylamino)-4-methylpent-2-ynethioate or a pharmaceutically acceptable salt thereof, and more particularly the 4-(Dimethylamino)-4-methyl-2-pentynethioic acid S-methyl ester fumarate, and a compound able to increase the $H_2O_2$ level in cancer cells of a subject.

In one embodiment, said cancer cells of said subject also have a MDA-adducts level above 75 ng per µg of total protein and/or a HNE-adducts level above 1 µg per µg of total protein, after in vitro treatment with a compound of formula (I) or a pharmaceutical acceptable salt thereof.

In one embodiment, the present invention also relates to a pharmaceutical composition comprising a compound of formula (I) or a pharmaceutically acceptable salt thereof, in particular the S-methyl 4-(dimethylamino)-4-methylpent-2-ynethioate or a pharmaceutically acceptable salt thereof, and more particularly the 4-(Dimethylamino)-4-methyl-2-pentynethioic acid S-methyl ester fumarate, and a compound able to increase the $H_2O_2$ level in cancer cells of a subject.

In one embodiment, the present invention also relates to a method for selecting a subject suffering from a cancer and who will most likely benefit from a treatment with a compound of formula (I) or a pharmaceutically acceptable salt thereof, in particular the S-methyl 4-(dimethylamino)-4-methylpent-2-ynethioate, or a pharmaceutically acceptable salt thereof, wherein said method comprises:
  a. measuring the $H_2O_2$ level in a cancer cells sample of said subject;
  b. comparing the resulting level of step a. with a control value; and
  c. measuring the GSH level in a cancer cells sample of said subject;
  wherein if:
  the $H_2O_2$ level of cancer cells sample of said subject is not higher than the control value, and
  the GSH level of said cancer cells sample of said subject is below 0.5 nmol for 25 000 cells,
  said method further comprises:
  d. treating said subject with a compound able to induce a $H_2O_2$ level higher than the control value;
  e. checking that the resulting $H_2O_2$ level of said subject is higher than the control value; and
  f. treating said subject with a compound of formula (I) or a pharmaceutically acceptable salt thereof, in particular the S-methyl 4-(dimethylamino)-4-methylpent-2-ynethioate, or a pharmaceutically acceptable salt thereof.

In one embodiment, said method comprises:
  a. measuring the $H_2O_2$ level in a cancer cells sample of said subject;
  b. comparing the resulting level of step a. with a control value;
  c. measuring the GSH level in a cancer cells sample of said subject; and/or
  c'. measuring the MDA-adducts and/or HNE-adducts level after an in vitro treatment with a compound of formula (I) according to the invention or a pharmaceutical acceptable salt thereof in a cancer cells sample of said subject;
  wherein if:
  the $H_2O_2$ level of cancer cells sample of said subject is not higher than the control value,
  the GSH level of said cancer cells sample of said subject is below 0.5 nmol for 25 000 cells, and/or the MDA-adducts level is above 75 ng per µg of total protein and/or the HNE-adducts level is above 1 µg per µg of protein,
said method further comprises:
  d. treating said subject with a compound able to induce a $H_2O_2$ level higher than the control value;
  e. checking that the resulting $H_2O_2$ level of said subject is higher than the control value; and
  f. treating said subject with a compound of formula (I) or a pharmaceutically acceptable salt thereof, in particular the S-methyl 4-(dimethylamino)-4-methylpent-2-ynethioate, or a pharmaceutically acceptable salt thereof.

Checking that the resulting $H_2O_2$ level of said subject is higher than the control value can be done by the above previously cited methods.

In particular, the compounds of the combination or products according to the invention are administered separately, sequentially or simultaneously.

More particularly, the compounds of the combination or products according to the invention are administered sequentially, the compound able to increase the $H_2O_2$ level in cancer cells of a subject, being administered prior to administration of the compound of formula (I) or a pharmaceutically acceptable salt thereof, in particular the S-methyl 4-(dimethylamino)-4-methylpent-2-ynethioate, or a pharmaceutically acceptable salt thereof, and more particularly the 4-(Dimethylamino)-4-methyl-2-pentynethioic acid S-methyl ester fumarate.

In one embodiment, the combination for use according to the invention or products for use according to the invention consists of a compound of formula (I) or a pharmaceutically acceptable salt thereof, in particular the S-methyl 4-(dimethylamino)-4-methylpent-2-ynethioate, or a pharmaceutically acceptable salt thereof, and more particularly the 4-(Dimethylamino)-4-methyl-2-pentynethioic acid S-methyl ester fumarate, and a compound able to increase the $H_2O_2$ level in cancer cells of a subject.

Compounds of the combinations, products and methods of the invention may be prepared by a variety of synthetic routes. The reagents and starting materials are commercially available, or readily synthesized by well-known techniques by one of ordinary skill in the arts.

The identification of the subjects who are in need of treatment of herein-described diseases and conditions is conducted as above mentioned and is well within the ability and knowledge of one skilled in the art. A clinician skilled in the art can readily identify, by the above mentioned techniques, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

As used herein, a "therapeutically effective amount" refers to an amount which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment and chronic use.

The amount of the compounds of the combination, products or methods according to the invention, which is required to achieve the desired biological effect, will vary depending upon a number of factors, including the dosage of the drug to be administered, the chemical characteristics (e.g. hydrophobicity) of the compounds employed, the potency of the compounds, the type of disease, the diseased state of the patient, and the route of administration.

Compounds provided herein can be formulated into pharmaceutical compositions, as above mentioned, by admixture with one or more pharmaceutically acceptable excipients.

As used herein, a "pharmaceutically acceptable excipient" refers to molecular entities and compositions that do not produce an adverse, allergic or other untoward reaction when administered to a mammal, especially a human, as appropriate. A pharmaceutically acceptable excipient refers to a non-toxic solid, semi-solid or liquid filler, diluent, encapsulating material or formulation auxiliary of any type.

Such compositions may be prepared for use in oral administration, particularly in the form of tablets or capsules, in particular orodispersible (lyoc) tablets; or parenteral administration, particularly in the form of liquid solutions, suspensions or emulsions.

It may be prepared by any of the methods well known in the pharmaceutical art, for example, as described in Remington: *The Science and Practice of Pharmacy,* 20th ed.; Gennaro, A. R., Ed.; Lippincott Williams & Wilkins: Philadelphia, Pa., 2000. Pharmaceutically compatible binding agents and/or adjuvant materials can be included as part of the composition. Oral compositions will generally include an inert diluent carrier or an edible carrier. They can be administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Liquid preparations for administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, acrylate copolymers, vegetable oils such as olive oil, and organic esters such as ethyl oleate. Aqueous carriers include mixtures of alcohols and water, hydrogels, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like.

Examples of modes of administration include parenteral e.g. subcutaneous, intramuscular, intravenous, intradermal, as well as oral administration. It includes in particular a formulation as a tablet for oral administration or as a powder for solution for injection for intravenous administration.

In the scope of the present invention, it has to be understood that "a combination comprising a compound of formula (I) and a compound able to increase the $H_2O_2$ level in cancer cells of a subject, for use" is equivalent to "the use of a combination comprising a compound of formula (I) or a pharmaceutically acceptable salt thereof and a compound able to increase the $H_2O_2$ level in cancer cells of a subject" and in particular that "a combination comprising a compound of formula (I) or a pharmaceutically acceptable salt thereof and a compound able to increase the $H_2O_2$ level in cancer cells of a subject, for use in the treatment of" is equivalent to "the use of a combination comprising a compound of formula (I) or a pharmaceutically acceptable salt thereof and a compound able to increase the $H_2O_2$ level in cancer cells of a subject, for the treatment of" and to "the use of a combination comprising a compound of formula (I) or a pharmaceutically acceptable salt thereof and a compound able to increase the $H_2O_2$ level in cancer cells of a subject, for the manufacture of a medicament intended for the treatment". The same applies for the products for use according to the invention.

BRIEF DESCRIPTION OF THE DRAWINGS

The present invention will be further illustrated by the following figures and examples.

FIGURES

Figure 1:
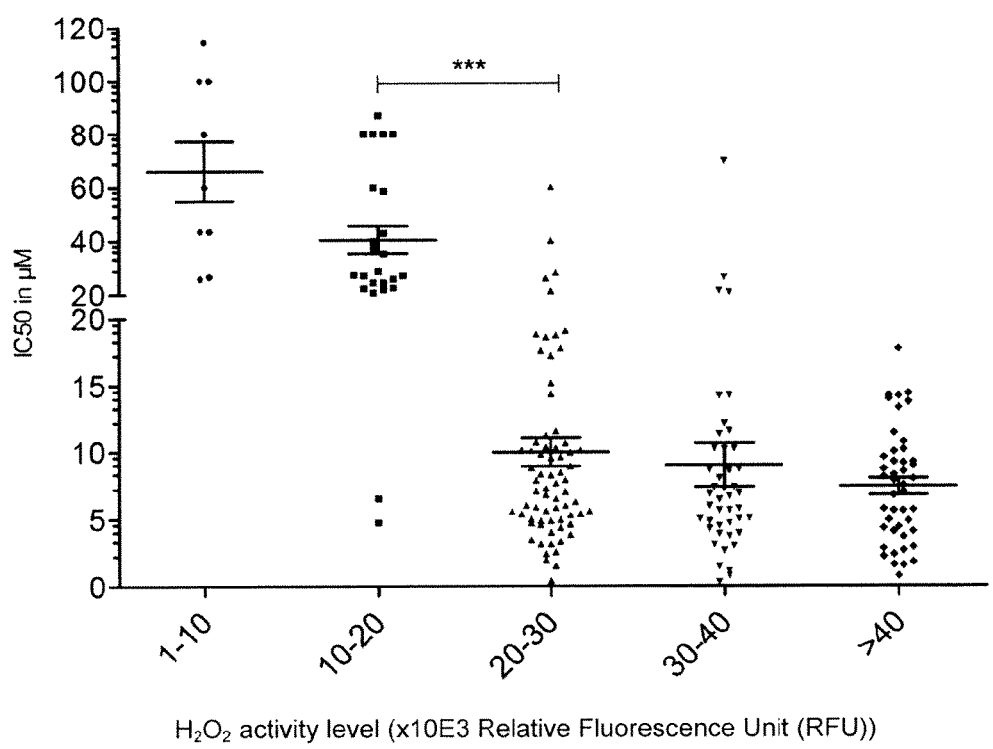

FIG. 1: $H_2O_2$/S-methyl 4-(dimethylamino)-4-methylpent-2-ynethioate $IC_{50}$ correlation: relationship between $IC_{50}$ of S-methyl 4-(dimethylamino)-4-methylpent-2-ynethioate in µM and the endogenous $H_2O_2$ activity levels in cancer cells FIG. 2: $H_2O_2$/S-methyl 4-(dimethylamino)-4-methylpent-2-ynethioate $IC_{50}$ correlation: Determination of a cut-off FIG. 3: $H_2O_2$/S-methyl 4-(dimethylamino)-4-methylpent-2-ynethioate $IC_{50}$ correlation: Studies by tissue origin FIGS. 4 to 6: $H_2O_2$/S-methyl 4-(dimethylamino)-4-methylpent-2-ynethioate $IC_{50}$ correlation: induction of sensitivity to S-methyl 4-(dimethylamino)-4-methylpent-2-ynethioate by increasing $H_2O_2$ activity (PCN=pyocyanin) on three cancer cells lines: THP-1, HCC827 and Hop62

Figure 7:
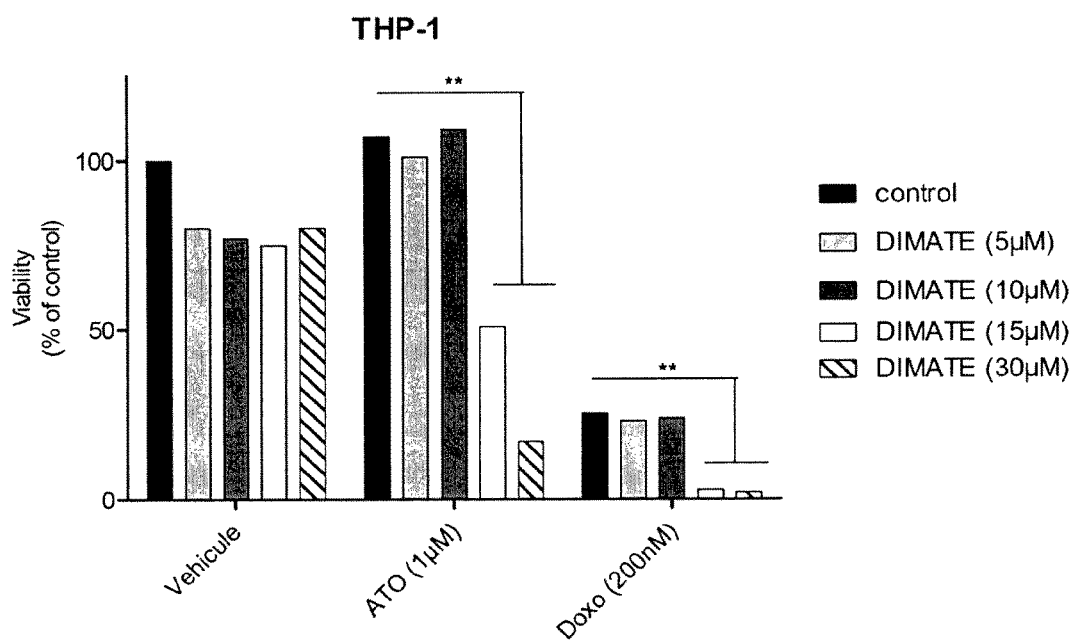

FIG. 7: $H_2O_2$/S-methyl 4-(dimethylamino)-4-methylpent-2-ynethioate $IC_{50}$ correlation: synergic effect of S-methyl 4-(dimethylamino)-4-methylpent-2-ynethioate and $H_2O_2$ inducer drugs: Arsenic trioxide (As2O3) (ATO) 1 µM and Doxorubicine (Doxo) 200 nM FIG. 8: Combination treatment using S-methyl 4-(dimethylamino)-4-methylpent-2-ynethioate and $H_2O_2$ inducing agent, Cisplatin (CPPD) or Doxorubicin (Doxo), in a context wherein cancer cells Colo357 have a level of GSH higher than 5 nmol for 25000 cells FIG. 9: Total GSH level in nmol per 25000 cells observed in sensitive and resistant cells FIG. 10: Quantification of MDA and HNE adducts in S-methyl 4-(dimethylamino)-4-methylpent-2-ynethioate sensitive cells (HL-60, NT2/D1) (A) and S-methyl 4-(dimethylamino)-4-methylpent-2-ynethioate resistant cells (MSC) treated with S-methyl 4-(dimethylamino)-4-methylpent-2-ynethioate 5 or 10 $\mu mol \cdot L^{-1}$ during 24 hours (B)

Note: in all the figures mentioned above: DIMATE is given for S-methyl 4-(dimethylamino)-4-methylpent-2-ynethioate.

DETAILED DESCRIPTION MATERIAL AND METHODS

Cell Lines

A panel of 52 human tumor cells representing 10 tissue types has been selected to cover a broad set of different oncogenes and according to their response to different standard chemotherapeutics. Cells were obtained from the American Type Culture Collection (ATCC), the European Collection of Cell Cultures (ECACC) and from primary culture of cancer cells derived from patients' tumors (Research Institute of Vall d'Hebron (VHIR), Barcelone, Spain; Vall d'Hebron Institute of Oncology (VHIO), Barcelone, Spain; Oncotest, Freiburg, Germany; Oncodesign, Dijon, France; Universitá, Degli Studi di Palermo, Oncology and Surgical Sciences, Palermo, Italy; and Institute of Predictive and Personalized Medicine of Cancer (IMPPC), Barcelona, Spain (See Table 3 for description of the tumor cell panel). All cells were cultivated in appropriate media according to supplier recommendations.

TABLE 3

| Tissue | Characteristics | Cells | Type of cell line |
|---|---|---|---|
| Bladder | | UM-UC-3 | established cell line |
| Bladder | | HT-1197 | established cell line |
| Bladder | | LB831-BLC | established cell line |
| Bladder | | RT112 | established cell line |
| Bladder | | T24 | established cell line |
| Blood | | HL-60 | established cell line |
| Blood | | OCI-AML2 | established cell line |
| Blood | | Raji | established cell line |
| Blood | | U-937 | established cell line |
| Blood | | Kasumi-1 | established cell line |
| Blood | | MOLM-14 | established cell line |
| Blood | | KG-1 | established cell line |
| Blood | | K-562/imatinib | established cell line |
| Blood | | THP-1 | established cell line |
| Brain | | CGL-1 | established cell line |
| Brain | | SK-N-AS | established cell line |
| Brain | | U-87 | established cell line |
| Brain | | BrGl2 | established cell line |
| Brain | | BrGl3 | established cell line |
| Brain | | BrGl6 | established cell line |
| Brain | | BrA1 | established cell line |
| Brain | | CGL-9 | established cell line |
| Breast | | SK-BR-3 | established cell line |
| Breast | | BT-20 | established cell line |
| Breast | | BT-474c | established cell line |
| Breast | | MCF-7 | established cell line |
| Breast | | MDA-MB-231 | established cell line |
| Breast | | MDA-MB-468 | established cell line |
| Breast | | BA-pt1102 | established cell line |
| Breast | | MBC-pt1106 | established cell line |

TABLE 3-continued

| Tissue | Characteristics | Cells | Type of cell line |
|---|---|---|---|
| Breast | | BA-pt1201 | established cell line |
| Breast | | BA-pt1202 | established cell line |
| Breast | | BA-pt1205 | established cell line |
| Cervix | | Hela | established cell line |
| Colon | | LoVo | established cell line |
| Colon | | SW620 | established cell line |
| Colon | | COLO-205 | established cell line |
| Colon | | HCT-15 | established cell line |
| Colon | | CRA07 | established cell line |
| Colon | | CRA11 | established cell line |
| Colon | | CRA13 | established cell line |
| Head & Neck | | LB1617-HNSCC | established cell line |
| Head & Neck | | Fadu | established cell line |
| Head & Neck | | KB | established cell line |
| Kidney | | Caki-1 | established cell line |
| Kidney | | A-498 | established cell line |
| Liver | | Hep G2 | established cell line |
| Liver | | Hep 3B2.1-7 | established cell line |
| Lung | | A-549 | established cell line |
| Lung | | A-549 | established cell line |
| Lung | | H-522 | established cell line |
| Lung | | PC-9 | established cell line |
| Lung | | HCC4006 | established cell line |
| Lung | | HCC2935 | established cell line |
| Lung | | H1975 | established cell line |
| Lung | | H1650 | established cell line |
| Lung | | H820 | established cell line |
| Lung | | H2935 | established cell line |
| Lung | | HCC4006 | established cell line |
| Lung | | HCC827 | established cell line |
| Lung | | H1299 | established cell line |
| Lung | | Hop62 | established cell line |
| Lung | | H522 | established cell line |
| Lung | | H23 | established cell line |
| Lung | | H460 | established cell line |
| Lung | | H441 | established cell line |
| Melanoma | | SKMEL-103 | established cell line |
| Melanoma | | SKMEL-147 | established cell line |
| Melanoma | | MLMN-9 | established cell line |
| Melanoma | | MLMN-10 | established cell line |
| Melanoma | | UACC-903 | established cell line |
| Melanoma | | SKMEL-28 | established cell line |
| Melanoma | | MBrM12 | established cell line |
| Muscle | | A-673 | established cell line |
| Normal | | HMVEC | established cell line |
| Normal | | HUV-EC-C | established cell line |
| Normal | | MRC-5 | established cell line |
| Normal | | HSC CD34+ | established cell line |
| Normal | | MSC | established cell line |
| Osteosarcoma | | OS-0411 | established cell line |
| Ovary | | PD-OVC-17 | established cell line |
| Ovary | | A2780 | established cell line |
| Ovary | | A2780/Cis | established cell line |
| Ovary | | IGROV-1 | established cell line |
| Ovary | | SK-OV-3 | established cell line |
| Ovary | | OVCAR-3 | established cell line |
| Ovary | | OVCAR-4 | established cell line |
| Ovary | | PD-OVC-11 | established cell line |
| Ovary | | PD-OVC-02 | established cell line |
| Ovary | | PD-OVC-05 | established cell line |
| Pancreas | | Capan-1 | established cell line |
| Pancreas | | Capan-2 | established cell line |
| Ovary | | PD-OVC-17 | established cell line |
| Pancreas | | MIA PaCa-2 | established cell line |
| Prostate | | 22Rv1 | established cell line |
| Prostate | | LNCap | established cell line |
| Prostate | | PC3 | established cell line |
| Prostate | | DU145 | established cell line |
| Stomach | | KATO III | established cell line |
| Bladder | | 1036 | PDC |
| Bladder | | 1218 | PDC |
| Bladder | | 1228 | PDC |
| Bladder | | 1258 | PDC |
| Bladder | | 1352 | PDC |
| Bladder | | 439 | PDC |
| Central Nervous System | | 498 | PDC |
| Cervix | | 1729 | PDC |

TABLE 3-continued

| Tissue | Characteristics | Cells | Type of cell line |
|---|---|---|---|
| Cervix | | 1783 | PDC |
| Cervix | | 2025 | PDC |
| Cervix | | 280 | PDC |
| Cervix | | 742 | PDC |
| Cervix | | 94 | PDC |
| Cervix | | 975 | PDC |
| Gastric | Asian | 3013 | PDC |
| Asian Gastric | Asian | 3044 | PDC |
| Asian Gastric | Asian | 3052 | PDC |
| Gastric | Caucasian | 1172 | PDC |
| Gastric | Caucasian | 214 | PDC |
| Gastric | Caucasian | 251 | PDC |
| Head and Neck; | Caucasian | 1842 | PDC |
| Lung | Adeno | 1041 | PDC |
| Lung | Adeno | 1584 | PDC |
| Lung | Adeno | 1647 | PDC |
| Lung | Adeno | 289 | PDC |
| Lung | Adeno | 526 | PDC |
| Lung | Adeno | 623 | PDC |
| Lung | Adeno | 629 | PDC |
| Lung | Adeno | 629 | PDC |
| Lung | Adeno | 923 | PDC |
| Lung | Adeno | 983 | PDC |
| Lung | Epidermoid | 1422 | PDC |
| Lung | Epidermoid | 397 | PDC |
| Lung | Large Cell | 1072 | PDC |
| Lung | Large Cell | 1121 | PDC |
| Lung | Large Cell | 1674 | PDC |
| Lung | Large Cell | 430 | PDC |
| Lung | Large Cell | 529 | PDC |
| Breast | | 1162 | PDC |
| Breast | | 1322 | PDC |
| Breast | | 1384 | PDC |
| Breast | | 583 | PDC |
| Breast | | 713 | PDC |
| Breast | | MX1 | established cell line |
| Melanoma | | 1765 | PDC |
| Melanoma | | 1792 | PDC |
| Melanoma | | 274 | PDC |
| Melanoma | | 276 | PDC |
| Melanoma | | 462 | PDC |
| Melanoma | | 520 | PDC |
| Melanoma | | 622 | PDC |
| Melanoma | | 672 | PDC |
| Ovarian | | 1023 | PDC |
| Ovarian | | 1353 | PDC |
| Ovarian | | 1544 | PDC |
| Ovarian | | 899 | PDC |
| Pancreas | | 1872 | PDC |
| Pancreas | | 1900 | PDC |
| Pancreas | | 1986 | PDC |
| Pancreas | | 2033 | PDC |
| Pancreas | | 2082 | PDC |
| Pancreas | | 2116 | PDC |
| Pancreas | | 546 | PDC |
| Prostate | | DU-145 | established cell line |
| Prostate | | MRI-H-1579 | established cell line |
| Prostate | | PC-3M | established cell line |
| Pleuramesothelioma | | 1752 | PDC |
| Pleuramesothelioma | | 541 | PDC |
| Renal | | 1114 | PDC |
| Renal | | 1183 | PDC |
| Renal | | 1393 | PDC |
| Renal | | 486 | PDC |
| Renal | | 616 | PDC |
| Sarcoma | | 1937 | PDC |
| Colon | | CXF 1297 | PDC |
| Colon | | CXF 243 | PDC |
| Colon | | CXF 280 | PDC |
| Colon | | CXF 647 | PDC |
| Colon | | CXF 676 | PDC |
| Gastric | Asian | GXA 3011 | PDC |
| Gastric | Asian | GXA 3023 | PDC |
| Gastric | Caucasian | GXF 97 | PDC |
| Head & Neck | Caucasian | HNXF 536 | PDC |
| Head & Neck | Caucasian | HNXF 908 | PDC |
| Lung | Adeno | LXFA 400 | PDC |
| Lung | Adeno | LXFA 586 | PDC |
| Breast | | MAXF 449 | PDC |
| Breast | | MAXF 508 | PDC |
| Breast | | MAXF 583 | PDC |
| Breast | | MAXF 713 | PDC |
| Breast | | MAXF MX1 | PDC |
| Melanoma | | MEXF 1829 | PDC |
| Melanoma | | MEXF 989 | PDC |
| Ovary | | OVXF 1023 | PDC |
| Ovary | | OVXF 1353 | PDC |
| Ovary | | OVXF 1544 | PDC |
| Ovary | | OVXF 899 | PDC |
| Pancreas | | PAXF 1998 | PDC |
| Pancreas | | PAXF 2005 | PDC |
| Pancreas | | PAXF 2045 | PDC |
| Pancreas | | PAXF 2046 | PDC |
| Pancreas | | PAXF 2053 | PDC |
| Pancreas | | PAXF 2059 | PDC |
| Pancreas | | PAXF 2094 | PDC |
| Pancreas | | PAXF 546 | PDC |
| Renal | | RXF 1220 | PDC |
| Renal | | RXF 1781 | PDC |
| Renal | | RXF 631 | PDC |
| Skin | | SXFS 117 | PDC |

Enhancement of sensitivity of cell line to S-methyl 4-(dimethylamino)-4-methylpent-2-ynethioate has been done using selected cell line due to their resistance to S-methyl 4-(dimethylamino)-4-methylpent-2-ynethioate. Lung cancer cell lines (HCC827, Hop62) and leukemia cell lines (THP-1) were obtained from the American Type Culture Collection (ATCC), the European Collection of Cell Cultures (ECACC). Cells were cultivated in appropriate media according to supplier recommendations.

Cell Viability Assay, 96 Well Format

Cells were seeded into 96-well cell culture plates at concentrations required to ensure approximately 80% confluence in control (untreated cells) at the end of experiment ($0.5 \times 10^4$-$5 \times 10^4$ cell/well). The sensitivity towards S-methyl 4-(dimethylamino)-4-methylpent-2-ynethioate was determined using different concentrations of the drug (from 0.01 to 100 µM). After 48 hours, the growth-inhibitory effect of the drug was analyzed using Rezasurin, according to manufactures instruction. To ensure good data quality and to minimize impact of pipetting errors, each particular drug concentration was assessed based on mean fluorescence intensity from 8 separate wells. The drug response was quantified by the half maximal inhibitory concentration ($IC_{50}$) for each particular cell line, and determined by non-linear regression analysis of log-dose/response curves. Cut-off value for resistance to S-methyl 4-(dimethylamino)-4-methylpent-2-ynethioate was determined statistically (>2 S.D. above the $IC_{50}$ geometric mean). The in-vitro threshold value for hypersensitivity to the drug has been defined as <$IC_{50}$ geometric mean.

Enhancement of Sensitivity of Cells to S-methyl 4-(dimethylamino)-4-methylpent-2-ynethioate by Increasing the Level of $H_2O_2$ In a different experiment, cells showing resistance to S-methyl 4-(dimethylamino)-4-methylpent-2-ynethioate (THP-1, HCC827, and Hop62) were challenged with $H_2O_2$ inducer. Cells were seeded as described above and incubated with S-methyl 4-(dimethylamino)-4-methylpent-2-ynethioate (from 0.01 to 100 µM) alone or S-methyl 4-(dimethylamino)-4-methylpent-2-ynethioate in combination with $H_2O_2$ inducer Pyocyanin (40 µM). After 48 h of incubation, cell viability was measure using the Rezasurin assay as described above.

Chemotherapeutic agents that are known to induce $H_2O_2$ in cells were challenged in association with S-methyl 4-(dimethylamino)-4-methylpent-2-ynethioate to treat S-methyl 4-(dimethylamino)-4-methylpent-2-ynethioate resistant cells (THP-1). Cells were seeded as described above and incubate S-methyl 4-(dimethylamino)-4-methylpent-2-ynethioate (5, 10, 15, 30 µM) alone or with other drugs used in chemotherapy and known as $H_2O_2$ inducer like 2-Metoxyestradiol (2-ME 100 µM), Arsenic Trioxide (ATO 1 µM), Daunorubicine (40 nM), Doxorubicine (20 nM), Etoposide (500 nM), Mitoxanthrone (50 nM), Parthenolide (100 nM) and Piperlongumine (2 µM). After 48 hours of incubation, cell viability was measured using Rezasurin Assay as described above.

Measurement of $H_2O_2$ Production

Intracellular $H_2O_2$ production in live cells was measured using Total ROS/superoxide detection kit (Enzo life science), following the manufacturer's instructions. The assay uses specific $H_2O_2$/RNS probes that upon reaction with $H_2O_2$ and RNS species are oxidized rapidly to highly fluorescent compounds. Fluorescence intensity is proportional to the total $H_2O_2$/RNS levels within the sample. The experimental tests were performed using untreated cells, or cells treated with S-methyl 4-(dimethylamino)-4-methylpent-2-ynethioate (1-5 uM), vehicle HEPES, $H_2O_2$ inducer pyocyanin (PCN, 500 uM) or $H_2O_2$ inhibitor N-acetyl-L-cysteine (NAC) [10 mM]. The day before the analysis, cells were seeded in 96-well black/clear bottom plates at a density of $2 \times 10^4$ in culture media according to cell suppliers instructions, supplemented with FBS (10% v/v), 10 units of penicillin/ml and 100 mg of streptomycin. Cells were kept at 37° C. in a humid atmosphere of 95% air: 5% $CO_2$ overnight. On the day of the analysis, cells media was replaced by 100 µL of phenol free-media supplemented as above, without any treatment, with S-methyl 4-(dimethylamino)-4-methylpent-2-ynethioate for 6 hours, vehicle HEPES for 6 hours, or with the different control agents PCN and NAC for 20 min. After the incubation period, wells were loaded with 100 µL of $H_2O_2$ Detection Solution, containing the respective treatment agent or controls and incubated for 60 min at 37° C. in the dark. Several wells were left without cells for the background fluorescence control measurements. Plates were read using Appliskan fluorescence microplate reader (Thermo Scientific) (ex=560 nm, Em=600). Data are expressed as the change in arbitrary fluorescence units produced from equal amount of cells and normalized to total protein input.

Statistical Analysis

Values are expressed as mean±SD or frequencies and proportions. Differences between groups were determined by unpaired t test, Chi-square, Fisher's exact test or ANOVA, where appropriate. $P<0.05$ was considered statistically significant. Analysis was performed using GraphPad prism version 5.0 (GraphPad software, San Diego Calif. USA) and JMP software version 12.01 (SAS Institute Inc. North Carolina USA).

Measurement of GSH Production

Cells were seeded in 96-well black walled plate ($5 \times 10^4$ cells/mL) and incubated overnight for attachment. The cells were treated either with vehicle, DMSO, BCNU 100 µM, S-methyl 4-(dimethylamino)-4-methylpent-2-ynethioate 20 µM, for 24 hours. The total glutathione was measured according to the instructions of the kit (GSH-Glo™ Promega) and results were obtained for 25 000 cells.

Quantitative Determination of FINE-Protein and MDA/Protein Adducts by ELISA

The formation of HNE-adducts and MDA-adducts was quantified with the Oxiselect HNE Adduct Elisa kit (Cell Biolabs, San Diego, Calif.) and the OxiSelect MDA Adduct ELISA Kit (Cell Biolabs), respectively. Briefly, after a treatment with S-methyl 4-(dimethylamino)-4-methylpent-2-ynethioate during 24 hours, cells were lysed by sonication in reducing SDS Sample Buffer. Homogenates were diluted to 10 µg protein/mL and adsorbed in 96-well protein binding plates by incubation at 37° C. for at least 2 hours. Wells were washed twice with PBS and incubated for an additional 2 hours at room temperature on an orbital shaker. Following three washes in PBS, 100 µL of anti-HNE antibody or anti-MDA antibody were added to the wells and incubated for 1 hour at room temperature. Subsequently, goat anti-rabbit secondary antibody-HRP conjugate (diluted 1/1000 with the assay diluent) was added and incubation continued for 1 hour. Wells were washed five times in PBS and HRP-substrate was added. Reaction was stopped with an acidic solution, and absorbance read on a microplate reader at 450 nm. The level of HNE-adducts and of MDA-adducts was determined by comparison with a standard curve prepared from HNE-BSA and MDA-BSA standards supplied by the manufacturer.

Results

The results obtained are shown in FIGS. 1 to 10.

FIG. 1 shows that a correlation is observed between the $H_2O_2$ activity and the $IC_{50}$ (monitoring by Total ROS/superoxide detection kit as mentioned above).

Figure 2:
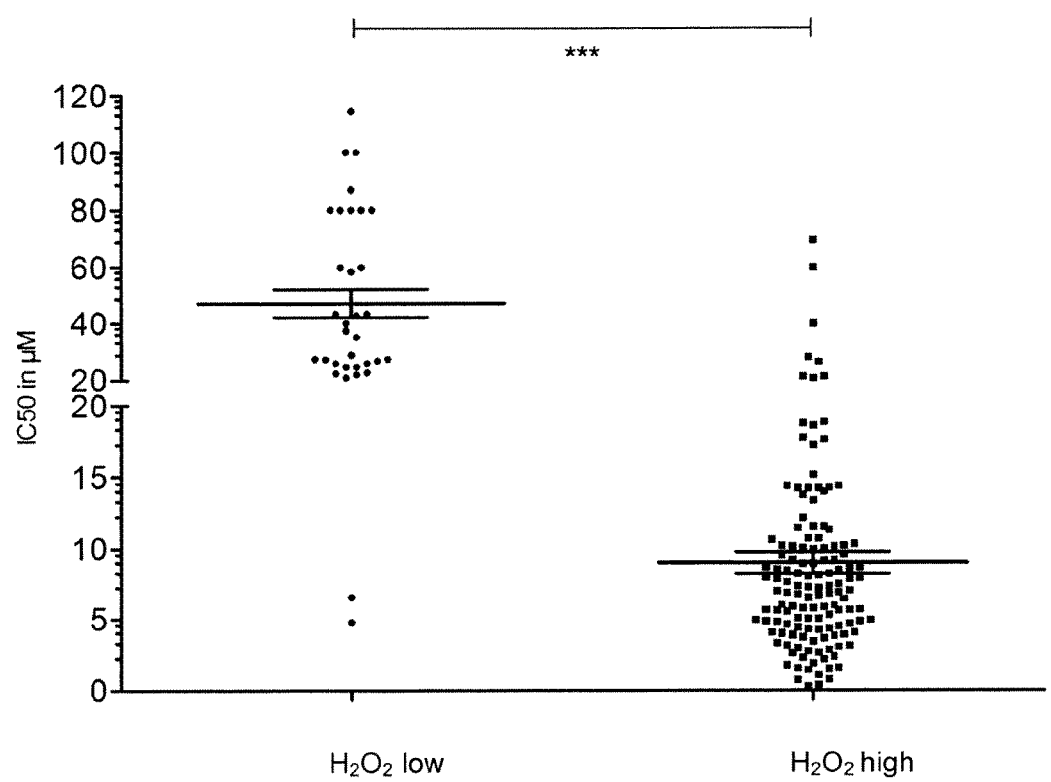

In addition, FIG. 2 shows that by separating the cells in two parts with a cut-off (20 000 Relative Fluorescence Intensity), a distinction of S-methyl 4-(dimethylamino)-4-methylpent-2-ynethioate sensibility of $H_2O_2$ high from $H_2O_2$ low is revealed (Pvalue<0.05).

Figure 3:
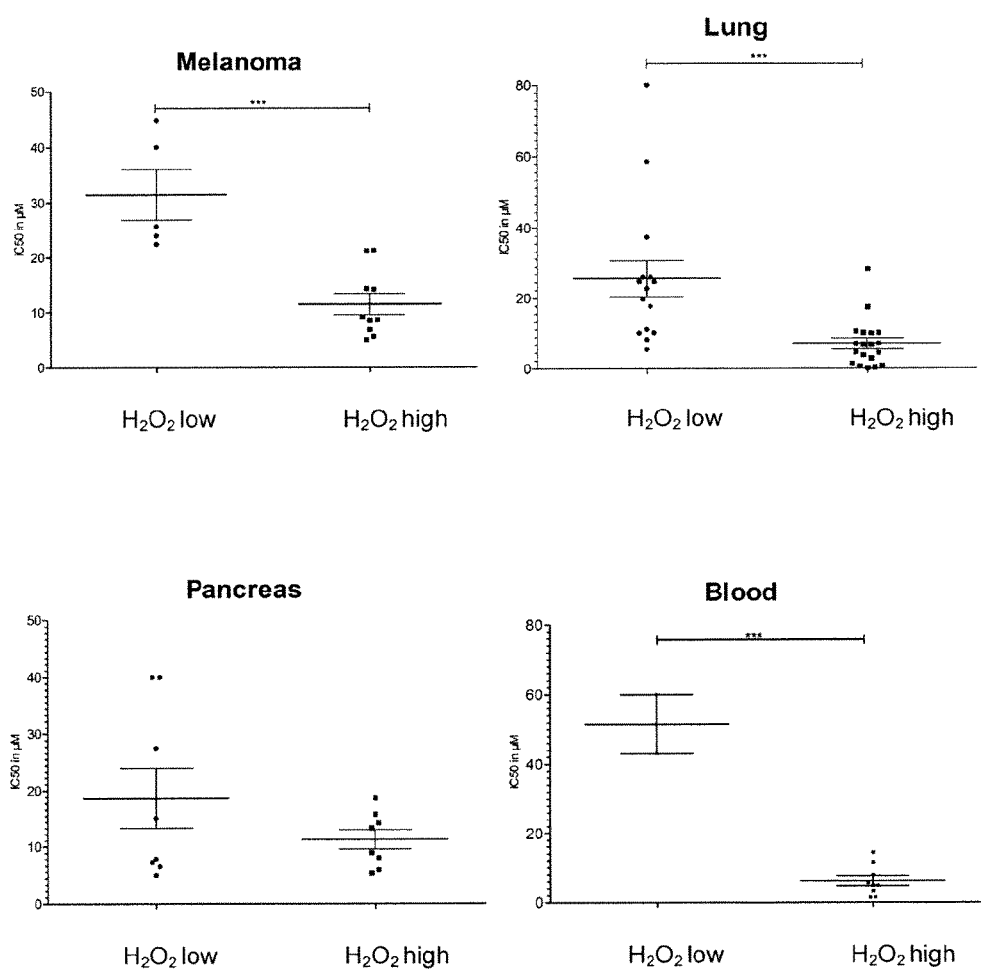

In FIG. 3, the correlation between $H_2O_2$ activity and $IC_{50}$ is illustrated by tissue origin.

Figure 4:
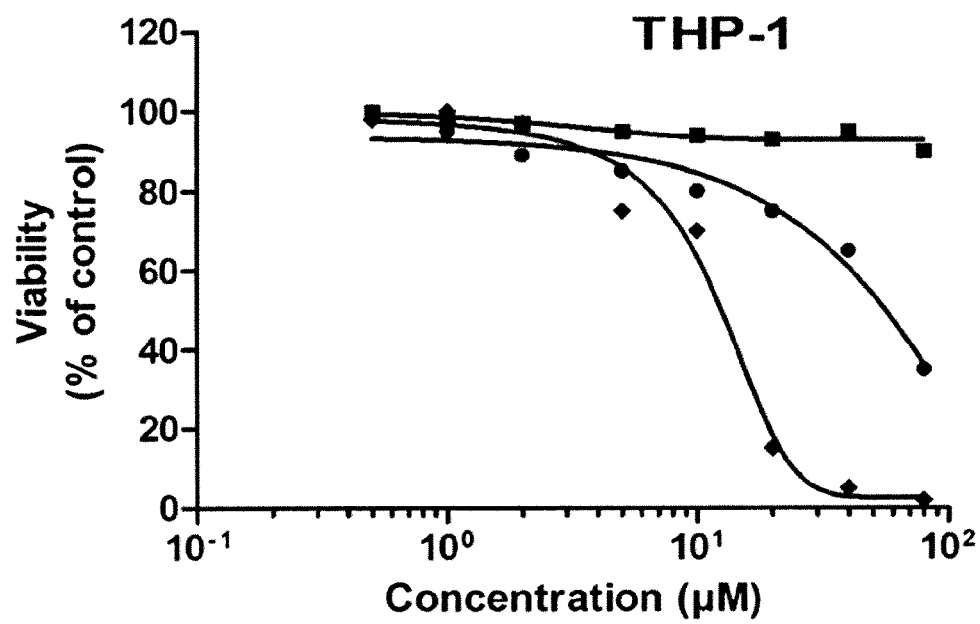
Figure 5:
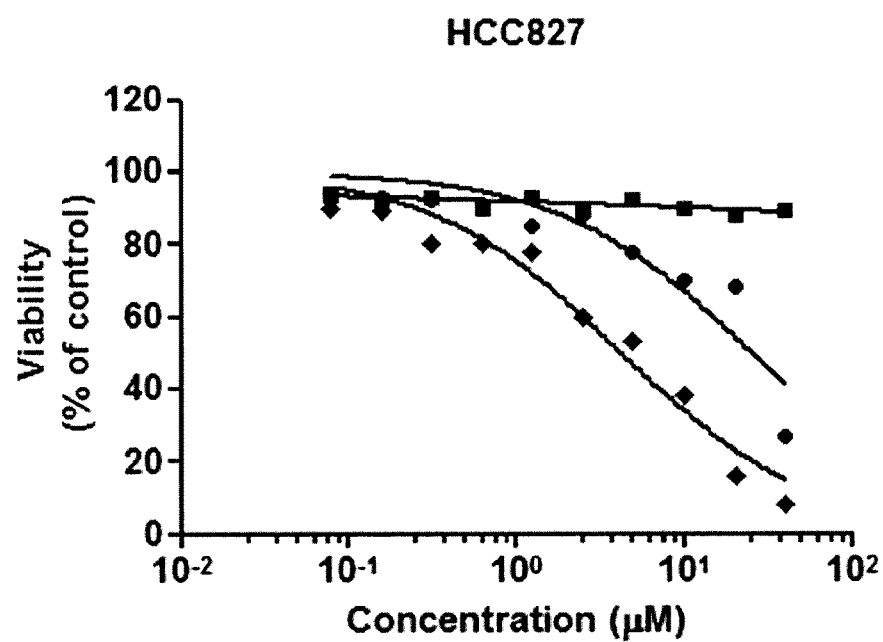
Figure 6:
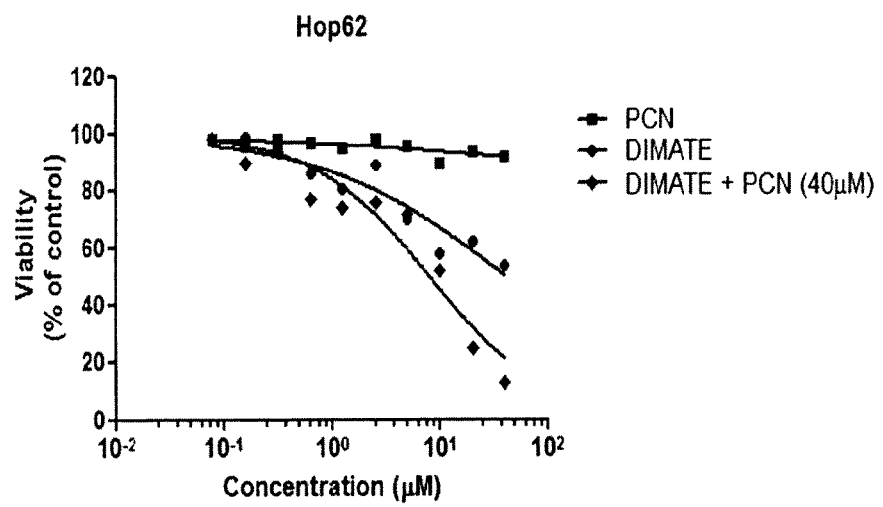

Furthermore, FIGS. 4 to 6 and the table 4 below show induction of sensibility to S-methyl 4-(dimethylamino)-4-methylpent-2-ynethioate using pre-treatment with pyocianin in a context wherein the cancer cells have a level of GSH below 5 nmol for 25000 cells.

TABLE 4

| | abs.$IC_{50}$ (µM) | | |
| --- | --- | --- | --- |
| | THP-1 | HCC827 | Hop62 |
| DIMATE | 46.0 | 24.98 | 39.0 |
| DIMATE + PCN (40 µM) | 10.59 | 4.92 | 8.98 |

DIMATE: S-methyl 4-(dimethylamino)-4-methylpent-2-ynethioate
PCN: pyocianin

Induction of sensibility to S-methyl 4-(dimethylamino)-4-methylpent-2-ynethioate was demonstrated using pre-treatment with pyocianin 40 µM. Cell exposure to pyocianin causes two-fold increase in $H_2O_2$ levels without affecting cell viability.

FIG. 7 shows a synergic effect with S-methyl 4-(dimethylamino)-4-methylpent-2-ynethioate and a compound able to increase the $H_2O_2$ level in cancer cells even in cells resistant to those compounds separately.

Furthermore, synergistic results were also shown with the combined treatment by S-methyl 4-(dimethylamino)-4-methylpent-2-ynethioate and the chemotherapeutic agents known to induce $H_2O_2$ on S-methyl 4-(dimethylamino)-4-methylpent-2-ynethioate THP-1 resistant cells, as shown in Table 5 below.

TABLE 5

|  | IC50 (µM) | P value |
|---|---|---|
| DIMATE + Etoposide | 25.22 | P < 0.001 |
| DIMATE + Mitoxanthrone | 22.67 | P < 0.001 |
| DIMATE + Daunorubicine | 12.5 | P < 0.001 |
| DIMATE + Parthnolide | 14.4 | P < 0.001 |
| DIMATE + Piperlongumine | 27.6 | P < 0.001 |
| DIMATE + Doxorubicine | 21.83 | P < 0.001 |
| DIMATE + ATO | 14.9 | P < 0.001 |
| DIMATE + 2-ME | <5 | P < 0.001 |
| DIMATE | 46 |  |

DIMATE: S-methyl 4-(dimethylamino)-4-methylpent-2-ynethioate

Figure 8:
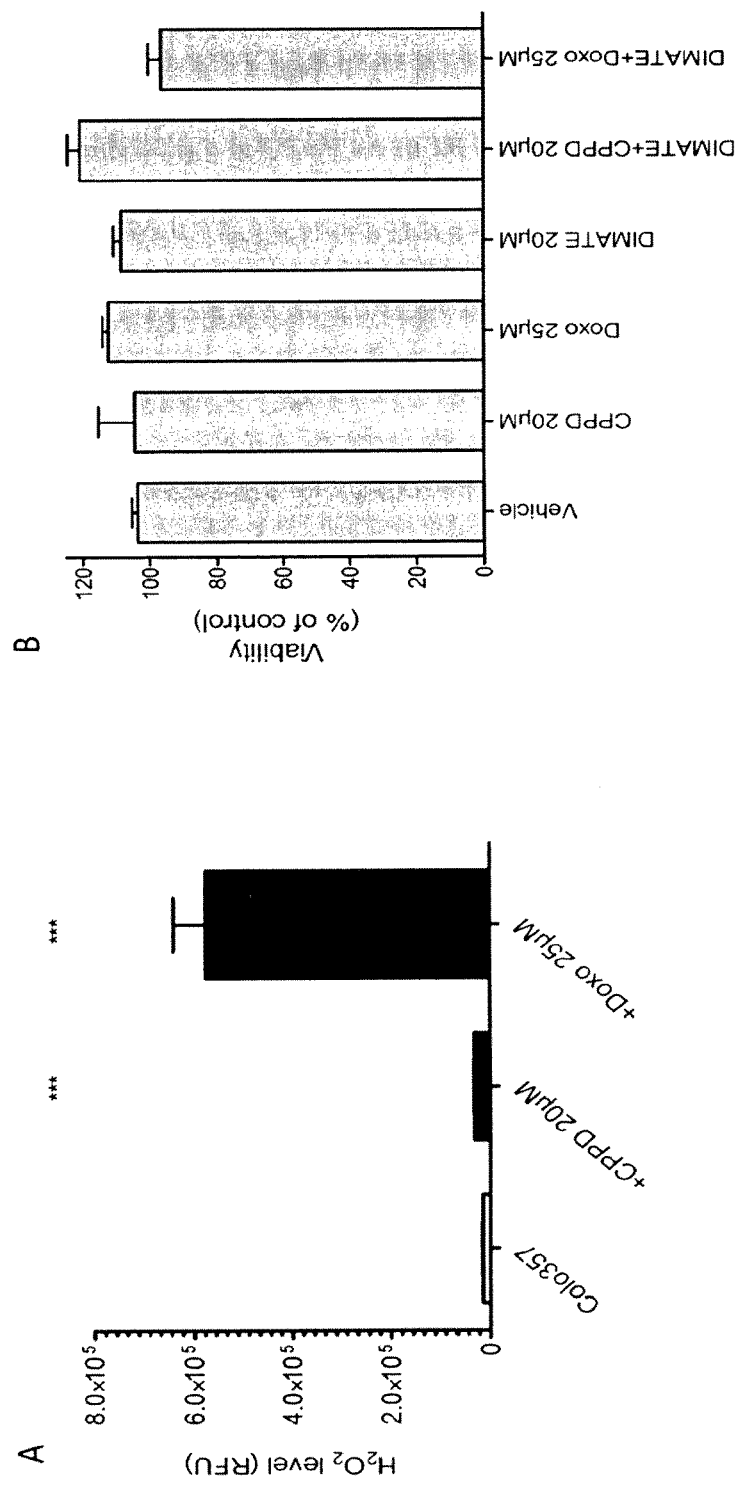

FIG. 8 relates to the combination treatment using S-methyl 4-(dimethylamino)-4-methylpent-2-ynethioate and $H_2O_2$ inducing agent, Cisplatin (CPPD) or Doxorubicin (Doxo), in a context wherein the cancer cells Colo357 have a level of GSH higher than 5 nmol for 25000 cells (contrary to what has been shown before).

It shows in FIG. 8(A) that the treatment using CPPD at 20 µmol·L−1 and Doxo at 25 µmol·L−1 increase significantly the $H_2O_2$ level in Colo357 cell line (respectively 200% and 10 000%) but that, as shown in FIG. 8 (B) no effect was however observed on viability.

Figure 9:
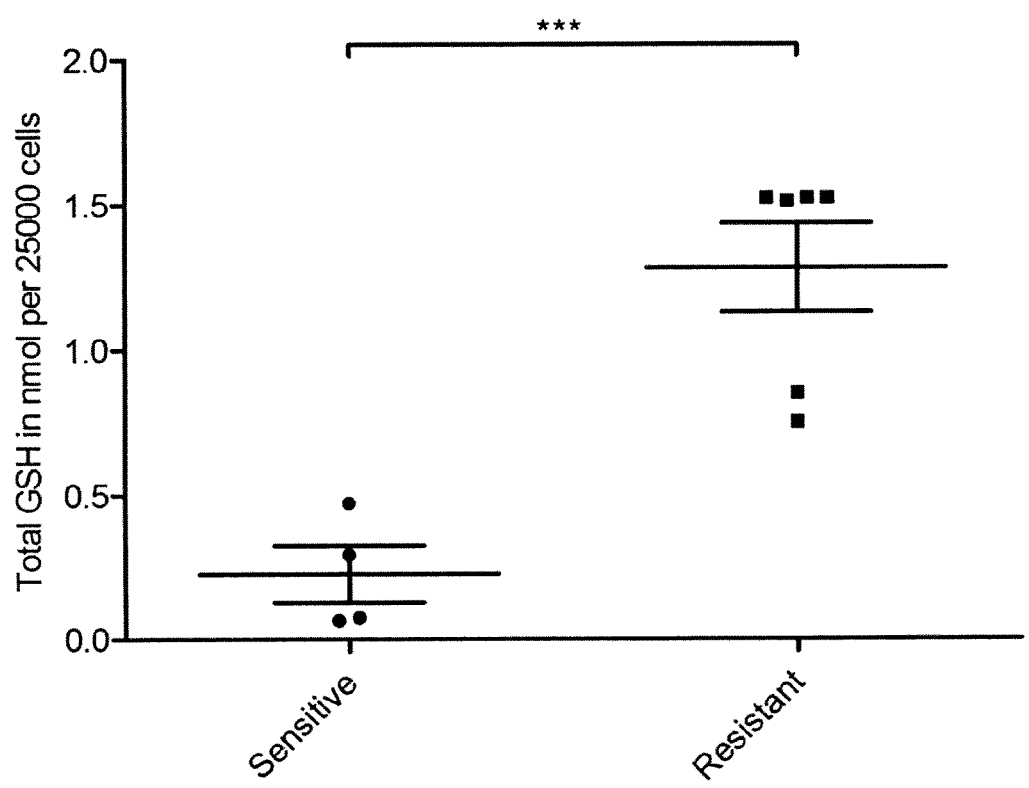
Figure 10:
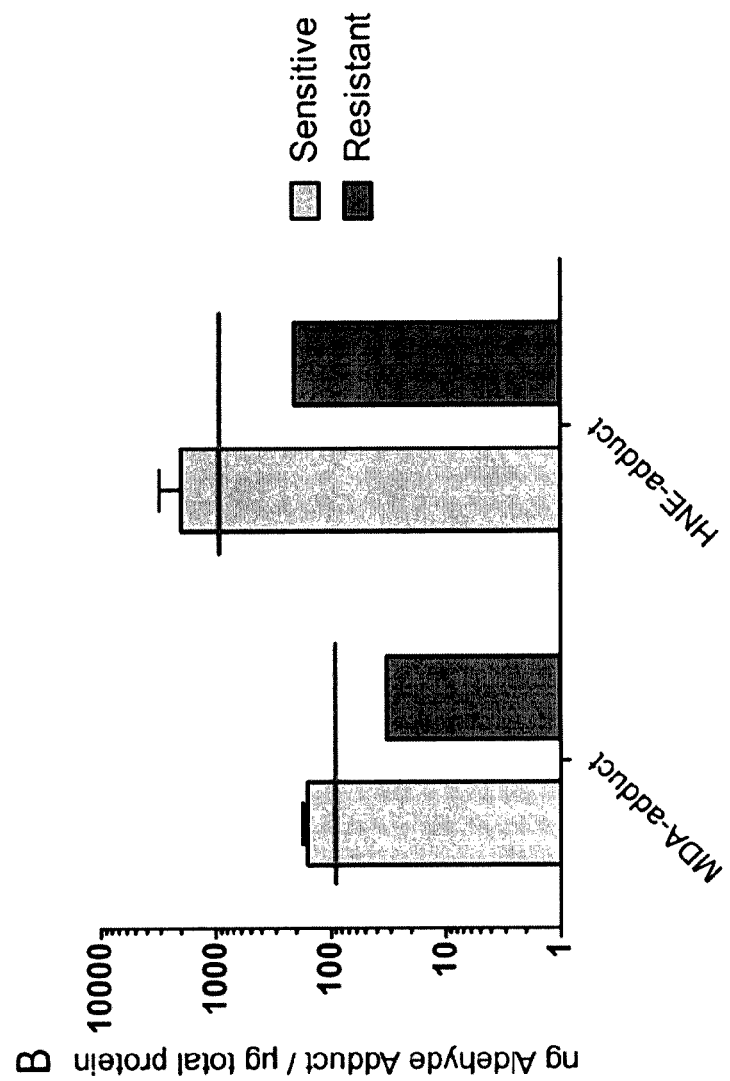
Figure 10:
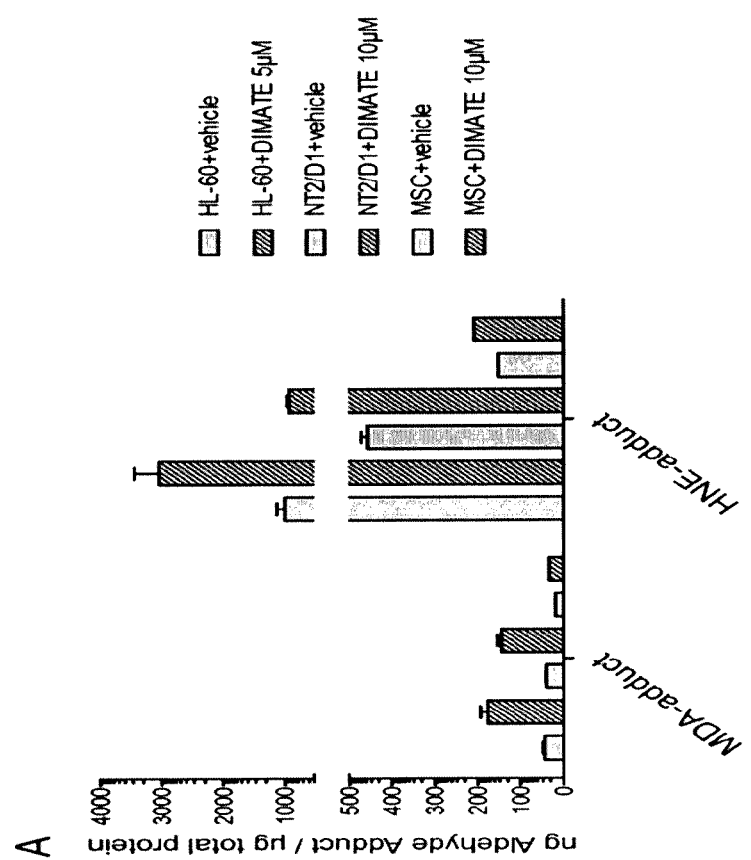

FIGS. 9 and 10 illustrate how the thresholds regarding GSH, MDA-adducts and HNE-adducts have been determined.

In FIG. 9, the total GSH level in nmol per 25000 cells is observed in sensitive and resistant cells. A significative difference (***, p-value<0.001) was observed. Using a threshold of 0.5 nmol per 25000 cells for distinction of GSH high from GSH low cells, 100% of sensitive cells are GSH low and 100% of resistant cells are GSH high.

FIG. 10 shows the quantification of MDA and HNE adduct in S-methyl 4-(dimethylamino)-4-methylpent-2-ynethioate sensitive cells (HL-60, NT2/D1) (A) and 5-methyl_4-(dimethylamino)-4-methylpent-2-ynethioate resistant cells (MSC) treated with S-methyl 4-(dimethylamino)-4-methylpent-2-ynethioate 5 or 10 µmol·L$^{-1}$ during 24 hours (B). For MDA-adducts, in sensitive S-methyl 4-(dimethylamino)-4-methylpent-2-ynethioate cells, the threshold is above 100 ng per µg of total protein, and in resistant cells, the threshold is below this threshold. For HNE-adducts, the same observation can be made with a threshold of 1 µg per µg of total protein.

The invention claimed is:

1. A method of treating cancer in a subject in need thereof, comprising administering a combination comprising a compound of formula (I):

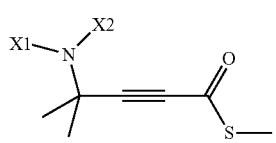

(I)

wherein X1 and X2, identical or different, are chosen among a $C_1$-$C_7$ alkyl group, a phenyl, a benzyl or X1 and X2 together with the nitrogen atom to which they are linked form an heterocycle;

or a pharmaceutical acceptable salt thereof; and a compound able to increase the $H_2O_2$ level in cancer cells of the subject, wherein the treatment is therapeutic, and wherein cancer cells of said subject:

do not overproduce $H_2O_2$ in comparison to a control value, and have a level of GSH below 0.5 nmol for 25 000 cells.

2. The method according to claim 1, wherein said method comprises measuring the $H_2O_2$ level and the GSH level in cancer cells of said subject, and wherein said $H_2O_2$ level is determined by quantifying the level of Fluorescence Intensity.

3. The method according to claim 1, further comprising the step of measuring a MDA-adducts level and/or a HNE-adducts level in a cancer cell sample of said subject after an in vitro treatment with the compound of formula (I) or a pharmaceutically acceptable salt thereof, wherein cancer cells of said subject after said treatment have MDA-adducts level above 75 ng per ng of total protein and/or a HNE-adducts level above 1 µg per µg of total protein.

4. A method for selecting a subject suffering from a cancer and who will most likely benefit from a treatment with a combination comprising a compound of formula (I):

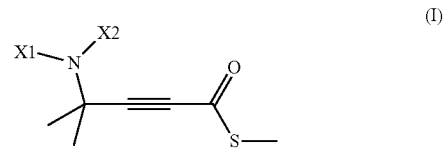

(I)

wherein X1 and X2, identical or different, are chosen among a $C_1$-$C_7$ alkyl group, a phenyl, a benzyl or X1 and X2 together with the nitrogen atom to which they are linked form an heterocycle;

or a pharmaceutical acceptable salt thereof; and a compound able to increase the $H_2O_2$ level in cancer cells of a subject, wherein said method comprises:

a) measuring the $H_2O_2$ level in a cancer cells sample of said subject;

b) comparing the resulting level of step a. with a control value; and c) measuring the GSH level in a cancer cells sample of said subject;

wherein:

a $H_2O_2$ level of said cancer cells sample of said subject not higher than the control value, and a GSH level of said cancer cells sample of said subject below 5 nmol for 25000 cells, indicates that the subject is likely to benefit from a treatment with a combination comprising a compound of formula (I), or a pharmaceutically acceptable salt thereof and a compound able to increase the $H_2O_2$ level in cancer cells of a subject.

5. The method according to claim 4, wherein said method comprises:

a) measuring the $H_2O_2$ level in a cancer cells sample of said subject;

b) comparing the resulting level of step a. with a control value;

d) measuring the GSH level in a cancer cells sample of said subject; and e) measuring the MDA-adducts and/or HNE-adducts level after an in vitro treatment with a compound of formula (I) in a cancer cells sample of said subject;

wherein:
a $H_2O_2$ level of said cancer cells sample of said subject not higher than the control value,
a GSH level of said cancer cells sample of said subject below 5 nmol for 25000 cells, and
a MDA-adducts level above 75 ng per µg of total protein and/or a HNE-adducts level above 1 µg per µg of protein,
indicates that the subject is likely to benefit from a treatment with a combination comprising a compound of formula (I), or a pharmaceutically acceptable salt thereof and a compound able to increase the $H_2O_2$ level in cancer cells of a subject.

6. The method according to claim 4, wherein a $H_2O_2$ level not higher than 20000 Relative Fluorescence Intensity, indicates that the subject is likely to benefit from a treatment with a combination comprising a compound of formula (I), or a pharmaceutically acceptable salt thereof and a compound able to increase the $H_2O_2$ level in cancer cells of a subject.

7. The method according to claim 3, wherein
the GSH level is determined by luminescence;
the MDA-adducts level and/or the HNE-adducts level is determined by immuno-monitoring; or
the cancer is chosen from leukemia, lymphomas, blood cancer, breast cancer, lung cancer, melanomas, colon cancer, pancreas cancer, ovarian cancer, osteosarcoma, brain cancer, bladder cancer and gastric cancer.

8. The method according to claim 1, wherein the compound of formula (I) is selected from the group consisting of:
a compound in which X1 and X2 are identical or different, and are chosen among a methyl, a phenyl, a benzyl, at least one of X1 or X2 being a methyl, or X1 and X2 together with the nitrogen atom to which they are linked form a piperidine or a morpholine;
S-methyl 4-(dimethylamino)-4-methylpent-2-ynethioate or a pharmaceutical acceptable salt thereof; and
4-(Dimethyl amino)-4-methyl-2-pentynethioic acid S-methyl ester fumarate.

9. The method according to 8, wherein
the GSH level is determined by luminescence;
the MDA-adducts level and/or the HNE-adducts level is determined by immuno-monitoring; or
the cancer is chosen from leukemia, lymphomas, blood cancer, breast cancer, lung cancer, melanomas, colon cancer, pancreas cancer, ovarian cancer, osteosarcoma, brain cancer, bladder cancer and gastric cancer.

10. The method according to claim 4, wherein the compound of formula (I) is selected from the group consisting of:
a compound in which X1 and X2 are identical or different, and are chosen among a methyl, a phenyl, a benzyl, at least one of X1 or X2 being a methyl, or X1 and X2 together with the nitrogen atom to which they are linked form a piperidine or a morpholine;
S-methyl 4-(dimethylamino)-4-methylpent-2-ynethioate or a pharmaceutical acceptable salt thereof; and
4-(Dim ethyl amino)-4-methyl-2-pentynethioic acid S-methyl ester fumarate.

* * * * *